(12) United States Patent
Kristensen et al.

(10) Patent No.: US 8,691,517 B2
(45) Date of Patent: Apr. 8, 2014

(54) FLEXIBLE CARBOHYDRATE-BEARING POLYMER

(75) Inventors: Jesper Svenning Kristensen, Virum (DK); Klaus Gregorius, Soborg (DK); Casper Struve, Kongens Lyngby (DK); Yihua Yu, Birkerod (DK)

(73) Assignee: Medtronic Minimed, Inc., Northridge, CA (US)

( * ) Notice: Subject to any disclaimer, the term of this patent is extended or adjusted under 35 U.S.C. 154(b) by 1406 days.

(21) Appl. No.: 12/085,961

(22) PCT Filed: Dec. 6, 2006

(86) PCT No.: PCT/EP2006/011708
§ 371 (c)(1),
(2), (4) Date: Sep. 11, 2008

(87) PCT Pub. No.: WO2007/065653
PCT Pub. Date: Jun. 14, 2007

(65) Prior Publication Data
US 2009/0187084 A1  Jul. 23, 2009

(30) Foreign Application Priority Data
Dec. 7, 2005 (WO) ................. PCT/EP2005/013114
Jun. 14, 2006 (GB) .................................. 0611773.3

(51) Int. Cl.
*G01N 33/543* (2006.01)
*G01N 33/542* (2006.01)
*G01N 33/66* (2006.01)
*A61B 5/145* (2006.01)

(52) U.S. Cl.
CPC .......... *G01N 33/66* (2013.01); *G01N 33/54373* (2013.01); *A61B 5/145* (2013.01); *A61B 5/14532* (2013.01)
USPC ........................... 435/7.93; 600/310; 536/18.5

(58) Field of Classification Search
CPC . G01N 33/66; G01N 33/54373; A61B 5/145; A61B 5/14532
See application file for complete search history.

(56) References Cited

U.S. PATENT DOCUMENTS

| | | | |
|---|---|---|---|
| 4,679,562 A | 7/1987 | Luksha | |
| 4,952,656 A | 8/1990 | Lai et al. | |
| 5,194,393 A | 3/1993 | Hugl et al. | |
| 5,277,872 A | 1/1994 | Bankert et al. | |
| 5,342,789 A | 8/1994 | Chick et al. | |
| 5,474,915 A | 12/1995 | Dordick et al. | |
| 5,476,776 A | 12/1995 | Wilkins | |
| 5,587,442 A | 12/1996 | Kiessling et al. | |
| 6,002,954 A | 12/1999 | Van Antwerp et al. | |
| 6,107,365 A | 8/2000 | Bertozzi et al. | |
| 6,232,130 B1 | 5/2001 | Wolf | |
| 6,256,522 B1 | 7/2001 | Schultz | |
| 6,271,315 B1 | 8/2001 | Kiessling et al. | |
| 6,485,703 B1 | 11/2002 | Cote et al. | |
| 6,538,072 B2 | 3/2003 | Kiessling et al. | |
| 6,927,246 B2 | 8/2005 | Noronha et al. | |
| 7,045,361 B2 | 5/2006 | Heiss et al. | |
| 7,297,548 B2 | 11/2007 | Kawanishi et al. | |
| 2002/0007016 A1* | 1/2002 | Kiessling et al. | .......... 525/326.1 |
| 2003/0125262 A1 | 7/2003 | Kiessling et al. | |
| 2003/0166136 A1 | 9/2003 | Bandman et al. | |
| 2003/0216300 A1 | 11/2003 | Cantor et al. | |
| 2004/0214190 A1 | 10/2004 | Butz et al. | |
| 2004/0248801 A1 | 12/2004 | Kiessling et al. | |
| 2004/0265898 A1 | 12/2004 | Afar et al. | |

FOREIGN PATENT DOCUMENTS

| | | | |
|---|---|---|---|
| EP | 0 561 653 | | 9/1993 |
| EP | 0 505 479 B1 | | 9/2001 |
| JP | 2005036254 A | * | 2/2005 |
| WO | WO 91/09312 | | 6/1991 |
| WO | WO 93/01498 | | 1/1993 |
| WO | WO 97/19188 | | 5/1997 |
| WO | WO 98/55869 | | 12/1998 |
| WO | WO 00/02048 | | 1/2000 |
| WO | WO 02/30275 A1 | | 4/2002 |
| WO | WO 02/46752 A2 | | 6/2002 |
| WO | WO 03/006992 A1 | | 1/2003 |
| WO | WO 03/031578 | | 4/2003 |
| WO | WO 2005/059037 A1 | | 6/2005 |
| WO | WO 2005/110207 A1 | | 11/2005 |
| WO | WO 2006/034081 | | 3/2006 |
| WO | WO 2006/061207 A1 | | 6/2006 |
| WO | WO 2006/061208 A1 | | 6/2006 |

OTHER PUBLICATIONS

Huber et al., "Carbohydrate Chemistry," In: Handbook of Food Science, Technology, and Engineering, vol. One, Chapter 1, edited by Y. H. Hui et al., CRC Press, 2006, pp. 1-1 and 1-11.*

(Continued)

*Primary Examiner* — Shafiqul Haq
*Assistant Examiner* — Galina Yakovleva
(74) *Attorney, Agent, or Firm* — Nixon & Vanderhye P.C.

(57) ABSTRACT

A sensor for the detection or measurement of a carbohydrate analyte in fluid comprises components of a competitive binding assay the readout of which is a detectable or measurable optical signal retained by a material that permits diffusion of the analyte but not the assay components, the assay components comprising: a carbohydrate binding molecule labelled with one of a proximity based signal generating/modulating moiety pair; and a carbohydrate analogue capable of competing with the analyte for binding to the carbohydrate binding molecule, the carbohydrate analogue being a flexible water-soluble polymer comprising: polymerized or co-polymerised residues of monomer units, the monomer unit residues bearing pendant carbohydrate or carbohydrate mimetic moieties and pendant moieties which are the other of the proximity based signal generating/modulating moiety pair.

24 Claims, 10 Drawing Sheets

(56) References Cited

OTHER PUBLICATIONS

A printout retrieved from http://en.wikipedia.org/wiki/Dextran on Feb. 22, 2013.*
JP 2005036254 A English Translation.*
Tyagi et al. Nature Biotechnology (1998) 18: p. 49.
Mantalto et al. 2001 J. Immunol. 166, 4148-4153.
Gestwicki et al. (2002) Chemistry and Biology 9, p. 163.
L. Tolosa et al, (1997) Analytical Chemistry 250, 102-108.
S. Fakirov et al, Makromol. Chem., 191, 603-614 (1990).
Pekari et al, J. Org. Chem., 2001, 66, 7432-7442.
Presanis et al, Biochemical Society Transactions (2003), vol. 31, part 4, 748-752.
Kiessling et al. (2000) Chapter 29: Principles for Multivalent Design, Ann. Rep. Med. Chem., p. 321-330.
Gestwicki et al., J. Am. Chem. Soc., 2002, 124, 14922-14933.
Yang et al., Carbohydrate Research, 337 (2002) 1605-1613.
Gordon et al., Nature vol. 392 Mar. 5, 1998, pp. 30-31.
Kanai et al., J. Am. Chem. Soc., 1997, 119, 9931-9932.
Lamanna et al., Journal of Bacteriology, Sep. 2002, p. 4981-4987.
Owen et al., Organic Letters 2002 vol. 4, No. 14 pp. 2293-2296.
I. Laursen et al. (2003) Mannan-binding lectin (MBL) production from human plasma, Biochem. Soc. Trans., 3 1(4), 758-762.
S.Chinnayelka and M. J. McShane (2004) Resonance Energy Transfer Nanobiosensors Based on Affinity Binding between Apo-Enzyme and Its Substrate, Biomacromolecules, 5, 1657-61.
Bahulekar R. et al., Biotechnology Techniques vol. 12 (10) 1998 721-724.
Ballerstadt et al. Sensors and Actuators B 38-39 (1997) 171-175.
Van Damme et al., Handbook of Plant Lectins: Properties and Biomedical Applications, Wiley & Sons, 1998, p. 142.
Ballerstadt et al., Diabetes Technology & Therapeutics, vol. 6, No. 2, 2004, pp. 191-200.
Disney et al.: "Detection of bacteria with carbohydrate-functionalized fluorescent polymers," Journal of the American Chemical Society, Washington, D.C., vol. 126, No. 41, Sep. 25, 2004, pp. 13343-13346, XP002366145.
Meadows et al.: "Design, Manufacture and Characterization of an Optical Fiber Glucose Affinity Sensor Based on an Homogeneous Fluorescence Energytransfer Assay System," Analytica Chimica Acta, Elsevier, Amsterdam, NL, vol. 280, 1993, pp. 21-30, XP001028148.
Ballerstadt et al.: "Competitive-Binding Assay Method Based on Fluorescence Quenching Ofligands Held in Close Proximity by a Multivalent Receptor," Analytica Chemica Acta, Elsevier, Amsterdam, NL, vol. 345, No. 1-3, 1997, pp. 203-212, XP000901095.
Cuihua Xue et al.: "Synthesis of Highly Water-Soluble Fluorescent Conjugated Glycopoly (P-Phenylenes)s for Lectin and *Escherichia coli*," ACM Transactions on Database Systems, ACM, New York, NY, vol. 7, No. 9, 2006, pp. 2470-2474, XP008076569, Biomacromolecules.
Lakowicz: "Measurement of Fluorescence Lifetimes", Chapter 3, Plenum Press, (1983), pp. 51-92.
Cerdan et al.: "Membranlektine von menschlichen Keratinozyten: Charakterisierung und Modulation deren Expression durch Zytokine", Parfumerie und Kosmetic, 74, Nr. 3/93, pp. 164-179.
Chang et al.: "Molecular characterization of human CD94: a type II membrane glycoprotein related to the C-type lectin superfamily", Eur. J. Immunol , (1995), vol. 25, pp. 2433-2437.
Kilpatrick et al.: "P35, an opsonic lectin of the ficolin family, in human blood from neonates, normal adults, and recurrent miscarriage patients", Immunology Letters 67, (1999), pp. 109-112,.
Itin et al.: "ERGIC-53 Is a Functional Mannose-selective and Calcium-dependent Human Homologue of Leguminous Lectins", Molecular Biology of the Cell, (Mar. 1996), vol. 7, pp. 483-493.
Christa et al.: "High expression of the human hepatocarcinoma-intestine-pancreas/pancreatic-associated protein (HIP/PAP) gene in the mammary gland of lactating transgenic mice", Eur. J. Biochem. 267, (2000), pp. 1665-1671.
Arce et al.: "The human C-type lectin CLECSF8 is a novel monocyte/macrophage endocytic receptor", Eur. J. Immunol , (2004), vol. 34, pp. 210-220.
Giorgino et al.: "The sentrin-conjugating enzyme mUbc9 interacts with GLUT4 and GLUT1 glucose transporters and regulates transporter levels in skeletal muscle cells", PNAS, (Feb. 1, 2000), vol. 97, No. 3, pp. 1125-1130.
Ehwald et al.: "Viscosimetric Affinity Assay", Analytical Biochemistry, (1996) vol. 234, No. 0040, pp. 1-8.
Beyer et al.: "Compensation of Temperature and Concanavalin a Concentratration Effects for Glucose Determination by the Viscometric Affinity Assay" Biotechnol. Prog. (2000), vol. 16, No. 6, pp. 1119-1123.

* cited by examiner

FLEXIBLE CARBOHYDRATE-BEARING POLYMER

This application is the U.S. national phase of International Application No. PCT/EP2006/011708 filed Dec. 6, 2006 which designated the U.S. and claims priority to International Application No. PCT/EP2005/013114 filed Dec. 7, 2005 and GB Application No. 0611773.3 filed Jun. 14, 2006, the entire contents of each of which are hereby incorporated by reference.

The present invention relates to a polymer bearing carbohydrate or carbohydrate mimetic moieties, to a method of preparing such a polymer, to a sensor comprising such a polymer, to a method of preparing such a sensor and to a method of using such a sensor.

The sensor may be used in the measurement or monitoring of carbohydrate in fluid, for example glucose in body fluid, using optical techniques.

The sensor is particularly suitable for use in situations in which glucose levels must be closely monitored and/or where glucose measurements must be taken repeatedly, such as in diabetes management.

In the management of diabetes, the regular measurement of glucose in the blood is essential in order to ensure correct insulin dosing. Furthermore, it has been demonstrated that in the long term care of the diabetic patient better control of the blood glucose levels can delay, if not prevent, the onset of retinopathy, circulatory problems and other degenerative diseases often associated with diabetes. Thus, there is a need for reliable and accurate self-monitoring of blood glucose levels by diabetic patients.

It is desirable to measure blood glucose over the range of concentrations which may occur in a diabetic patient, that is, from 0 to 35 mM or even higher.

Currently, blood glucose is monitored by diabetic patients with the use of commercially available colorimetric test strips or electrochemical biosensors (e.g. enzyme electrodes), both of which require the regular use of a lancet-type instrument to withdraw a suitable amount of blood each time a measurement is made. On average, the majority of diabetic patients would use such instruments to take a measurement of blood glucose twice a day. However, the US National Institute of Health has recommended that blood glucose testing should be carried out at least four times a day, a recommendation that has been endorsed by the American Diabetes Association. This increase in the frequency of blood glucose testing imposes a considerable burden on the diabetic patient, both in financial terms and in terms of pain and discomfort, particularly in the long-term diabetic who has to make regular use of a lancet to draw blood from the fingertips. Thus, there is clearly a need for a better long-term glucose monitoring system that does not involve drawing blood from the patient.

There have been a number of proposals for glucose measurement techniques that do not require blood to be withdrawn from the patient.

It has been observed that the concentration of analytes in subcutaneous fluid correlates with the concentration of said analytes in the blood, and consequently there have been several reports of the use of glucose monitoring devices which are sited in a subcutaneous location. The use of competitive binding assays for glucose which can be remotely interrogated is of particular interest.

A method of assaying a competitive binding is to use a proximity-based signal generating/modulating moiety pair (discussed in U.S. Pat. No. 6,232,120), which is typically an energy transfer donor-acceptor pair (comprising an energy donor moiety and an energy acceptor moiety). The energy donor moiety is photoluminescent (usually fluorescent).

In such methods, an energy transfer donor-acceptor pair is brought into contact with the sample (such as subcutaneous fluid) to be analyzed. The sample is then illuminated and the resultant emission detected. Either the energy donor moiety or the energy acceptor moiety of the donor-acceptor pair is bound to a receptor carrier (for example a carbohydrate binding molecule), while the other part of the donor-acceptor pair (bound to a ligand carrier, for example a carbohydrate analogue) and any analyte (for example carbohydrate) present compete for binding sites on the receptor carrier. Energy transfer occurs between the donors and the acceptors when they are brought together, which produces a detectable lifetime change (reduction) of the fluorescence of the energy donor moiety. Also, a proportion of the fluorescent signal emitted by the energy donor moiety is quenched.

The lifetime change is reduced or even eliminated by the competitive binding of the analyte. Thus, by measuring the apparent luminescence lifetime, for example, by phase-modulation fluorometry or time-resolved fluorometry (see Lakowicz, Principles of Fluorescence Spectroscopy, Plenum Press, 1983, Chapter 3), the amount of analyte in the sample can be determined.

It is to be noted that the efficiency of the energy transfer depends on the quantum yield of the donor, the overlapping of the emission spectrum of the donor with the absorption spectrum of the acceptor, and the relative distance and orientation between the donor and the acceptor.

In EP0561653 a method of interrogating a receptor and a ligand as described above is disclosed.

An example of donor-acceptor energy transfer is fluorescence resonance energy transfer (Förster resonance energy transfer, FRET), which is non-radiative transfer of the excited-state energy from the initially excited donor (D) to an acceptor (A). The donor typically emits at shorter wavelengths, and its emission spectrum overlaps with the absorption spectrum of the acceptor. Energy transfer occurs without the appearance of a photon and is the result of long-range dipole-dipole interactions between the donor and acceptor.

The term resonance energy transfer (RET) is more correct because the FRET process does not involve the appearance of a photon. However, FRET and RET are often used interchangeably.

An important characteristic of FRET is that it occurs over distances comparable to the dimensions of biological macromolecules. The distance at which FRET is 50% efficient, called the Förster distance, is typically in the range of 20-60 Å. Förster distances ranging from 20 to 90 Å are convenient for competitive binding studies.

Labelling an analyte-binding moiety with a donor (D) and an analyte analogue with an acceptor (A), or vice versa, would create an assay capable of generating a measurable response based on the donor-to-acceptor distance. Thus, binding of the D-"analyte-binding moiety" to A-"analyte analogue" results in a decrease in donor intensity or lifetime. The analyte in the sample competes for the analyte-binding moieties on D-"analyte-binding moiety", releasing D-"analyte-binding moiety" from the acceptor (A). The intensity decay time and phase angles of the donor are thus expected to increase with increasing glucose concentration.

These principles have been used in glucose sensing by energy transfer.

WO91/09312 describes a subcutaneous method and device that employs an affinity assay based on glucose (incorporating an energy transfer donor-acceptor pair) that is interrogated remotely by optical means. Examples WO97/19188, WO00/02048, WO03/006992 and WO02/30275 each describe glucose sensing by energy transfer, which produce an optical signal that can be read remotely.

A person skilled in the art will appreciate that the acceptor could be a fluorophore. Any fluorescent signal emitted by the energy acceptor moiety following excitation with a beam of incident radiation at a wavelength within the absorption spectrum of the energy acceptor moiety is unaffected by the FRET process. It is therefore possible to use the intensity of the fluorescent signal emitted by the energy acceptor moiety as an internal reference signal, for example in continuous calibration of the sensor or to monitor the extent to which the sensor has degraded and thus indicate the need to implant or inject a fresh sensor. The fall of this signal below an acceptable baseline level would indicate the need to implant or inject a fresh sensor.

The energy acceptor moiety may, however, be a non-fluorescent dye. In this case a compound with fluorescence quenching capability is used instead of the specific energy acceptor moiety. An example of a powerful and non-specific fluorescence quencher is given by Tyagi et al. Nature Biotechnology (1998) 18: p 49.

The systems discussed above rely on the plant lectin Concanavalin A (Con A) as the carbohydrate binding molecule. The present inventors have suggested in PCT/EP2005/013114 (WO06/061207) (from which priority is claimed) that animal lectins such as mannose binding lectin (MBL) could be used instead.

The term "lectin" includes any carbohydrate binding protein not obviously involved in carbohydrate metabolism and which does not belong to any of the major classes of immunoglobulins. Lectins show selective binding to carbohydrates via carbohydrate recognition domains (CRDs).

The present inventors have appreciated that the parameters which affect avidity of a carbohydrate analogue for a given carbohydrate binding molecule (in particular a lectin) include:
  number of carbohydrate (or carbohydrate mimetic) moieties
  affinity of the carbohydrate (or carbohydrate mimetic) moieties for the carbohydrate binding molecule
  calcium concentration (at least for MBL)
  flexibility of the carbohydrate analogue.

Physiological calcium concentration cannot be controlled. However, the other parameters can be selected to give a carbohydrate analogue with an appropriate measurement range. The effect of carbohydrate analogue flexibility on assay performance has not previously been identified or addressed.

Control of the first two variables is discussed in PCT/EP2005/013114 (WO06/061207) and PCT/EP2005/013115 (WO06/061208). Strong binding to MBL and other lectins is the result of binding at a number of sites. The binding at each site is relatively weak (low affinity) but the cumulative effect is strong binding (high avidity). Thus, a carbohydrate analogue which does not bind all the binding sites is more readily displaced by carbohydrate analyte, which binds all the binding sites, than a carbohydrate analogue which does bind all the binding sites. This explains why a carbohydrate analogue containing mannose, which has a higher affinity for MBL than does glucose, can be displaced by glucose.

Previously disclosed carbohydrate analogues (e.g. those of U.S. Pat. No. 6,232,130) have comprised globular proteins to which carbohydrate and energy donor or energy acceptor moieties are conjugated. In such molecules the carbohydrate and energy donor or energy acceptor moieties have fixed positions. This means that the carbohydrate analogues cannot necessarily adopt a conformation which allows binding of a plurality of carbohydrate moieties to lectin CRDs.

Also, the relative positioning of the carbohydrate and energy donor or energy acceptor moieties in such carbohydrate analogues may not allow optimum interaction between the energy donor and acceptor moieties when the analyte analogue and carbohydrate binding moiety are bound. This will affect FRET and weaken the optical signal.

Finally, these carbohydrate analogues often do not bind to lectins at physiological calcium concentrations (typically 1.15 to 1.29 mM). The calcium concentration required for optimum binding of mannose glycoconjugates to MBL has been found to be around 20 mM.

Carbohydrate polymers (e.g. optionally derivatised dextran and mannan) have also been used as carbohydrate analogues. In PCT/EP2005/013114 (WO06/061207) the use of periodate cleavage to allow binding of dextran to MBL at physiological calcium concentrations is disclosed.

However, the synthesis of such dextran derivatives is complicated (particularly as amine groups also need to be introduced to allow the energy donor or acceptor to be bonded to the carbohydrate analogue, and this can lead to cross-linking which causes undesirable precipitation).

Also, the fact that the carbohydrate moieties are the backbone structural units of carbohydrate polymers means that the number of carbohydrate moieties cannot readily be controlled. It has been found by the inventors that certain dextran derivatives are not readily displaced from MBL by glucose at physiological glucose concentrations, so that assay sensitivity is low.

Finally, binding to MBL at physiological calcium concentrations is still rather weak.

The present inventors have now developed a new type of analogue for glucose or other carbohydrate.

In a first aspect, the invention relates to a sensor for the detection or measurement of a carbohydrate analyte in fluid, the sensor comprising components of a competitive binding assay the readout of which is a detectable or measurable optical signal retained by a material that permits diffusion of the analyte but not the assay components, the assay components comprising:
  a carbohydrate binding molecule labelled with one of a proximity based signal generating/modulating moiety pair; and
  a carbohydrate analogue capable of competing with the analyte for binding to the carbohydrate binding molecule, the carbohydrate analogue being a flexible water-soluble polymer comprising:
  polymerized residues of monomer units, the monomer unit residues bearing pendant carbohydrate or carbohydrate mimetic moieties and pendant moieties which are the other of the proximity based signal generating/modulating moiety pair; and/or
  co-polymerised residues of first monomer units and second monomer units, the first monomer unit residues bearing pendant carbohydrate or carbohydrate mimetic moieties and the second monomer unit residues bearing pendant moieties which are the other of the proximity based signal generating/modulating moiety pair.

In a second aspect, the invention relates to a method of producing a polymer as described above, comprising one of the following procedures:
  a) polymerising monomer units each bearing a pendant carbohydrate or carbohydrate mimetic moiety and a pendant proximity based signal generating/modulating moiety and optionally third monomer units;

b) co-polymerising first monomer units each bearing a pendant carbohydrate or carbohydrate mimetic moiety and second monomer units each bearing a pendant proximity based signal generating/modulating moiety and optionally third monomer units;

c) polymerising monomer units each bearing a pendant carbohydrate or carbohydrate mimetic moiety and a pendant functional group for linking to an proximity based signal generating/modulating moiety and optionally third monomer units, then reacting the monomer unit residues with the proximity based signal generating/modulating moieties;

d) co-polymerising first monomer units each bearing a pendant carbohydrate or carbohydrate mimetic moiety and second monomer units each bearing a pendant functional group for linking to an proximity based signal generating/modulating moiety and optionally third monomer units, then reacting the second monomer unit residues with the proximity based signal generating/modulating moieties;

e) polymerising monomer units each bearing a pendant functional group for linking to a carbohydrate or carbohydrate mimetic moiety and a pendant different functional group for linking to an proximity based signal generating/modulating moiety and optionally third monomer units, then reacting the monomer unit residues with the carbohydrate or carbohydrate mimetic moieties and proximity based signal generating/modulating moieties; or f) co-polymerising first monomer units each bearing a pendant functional group for linking to a carbohydrate or carbohydrate mimetic moiety and second monomer units each bearing a pendant different functional group for linking to an proximity based signal generating/modulating moiety and optionally third monomer units, then reacting the first monomer unit residues with the carbohydrate or carbohydrate mimetic moieties and the second monomer unit residues with proximity based signal generating/modulating moieties.

An analogous method of producing a polymer wherein proximity based signal generating/modulating moieties are present in the single or the second monomer units before polymerization and carbohydrate or carbohydrate mimetic moieties are introduced after polymerization is also within the scope of the invention, but is not preferred.

Preferably, the analyte is a monosaccharide. In a preferred embodiment, the analyte is glucose.

Preferably, the sensor is suitable for the detection or measurement of glucose in body fluid, for example subcutaneous fluid. It is desirable for the sensor to be suitable for use in vivo, and this is discussed in more detail below.

Preferably, the carbohydrate analogue is capable of competing with glucose at physiological calcium concentrations.

Carbohydrate Analogue

The term "carbohydrate" includes sugars.

Preferably, the assay is capable of measuring blood glucose for concentrations over at least part of the range of 0 to 35 mM glucose, for example over the range of 0 to 25 mM glucose. Suitably, the $IC_{50}$ value is around 15 mM glucose. More preferably, the assay is capable of measuring glucose concentrations over the range of 2 to 10 mM glucose. A dosage-response curve which is as close as possible to linear within this range is desirable.

Synthesis of an artificial polymer rather than derivatisation of a protein or polysaccharide allows the parameters of the polymer (for example molecular flexibility, water solubility, molecular weight, nature of carbohydrate or carbohydrate mimetic moieties, number of carbohydrate or carbohydrate mimetics moieties, number of proximity based signal generating/modulating moieties) to be readily controlled to improve assay performance. Compared with a polysaccharide, a synthetic polymer has the advantage that the number of carbohydrate moieties can be controlled independently of the length of the polymer. Furthermore, using non-ring containing monomers such as 2-hydroxyethyl acrylate (HEA) in the polymer gives increased molecular rotational flexibility compared with dextran.

Without wishing to be bound by this theory, as mentioned above the inventors believe that it is important that proximity based signal generating/modulating moieties are close to the binding moiety to generate a strong signal. Globular ligands concentrate binding moieties and proximity based signal generating/modulating moieties on a spherical surface so that they are close. In dextran, which is linear, the backbone consists of binding moieties, and consequently it is not possible to control whether binding is close to or remote from a proximity based signal generating/modulating moiety. This can be controlled in the synthetic polymer by positioning the binding moieties close to the proximity based signal generating/modulating moieties.

Preferably, therefore, the polymer has a non-carbohydrate backbone.

The term "flexible" includes polymers which are capable of significant intermonomeric rotation. Preferably, the polymers do not contain bulky groups (for example ring structures, tert-butyl groups or other sterically large groups) other than the pendant carbohydrate or carbohydrate mimetic moieties and proximity based signal generating/modulating moieties. Preferably, such polymers have very few double bonds in the backbone structure (for example less than 10%). Suitably, such polymers do not have a globular tertiary structure, although they may have such a structure.

Preferably, the polymer is unbranched. This improves flexibility of the polymer. However, the polymer may be branched or cross-linked to some extent provided that this does not lead to formation of a hydrogel. For example, 1 to 5 branchings in a polymer with an overall molecular weight of 100 kDa is acceptable.

The term "water soluble" includes polymers having a water solubility at room temperature of at least 4 mg/ml, preferably at least 25 mg/ml, more preferably at least 50 mg/ml, for example at least 100 mg/ml. The solubility will be higher at body temperature. It is important that the polymer is water soluble so that it will dissolve in interstitial fluid when used in a sensor in the body as discussed below. The polymer should be water soluble even when bound to a carbohydrate binding molecule such as MBL.

Preferably, the polymer includes no more than 1 to 5 types of monomer unit, more preferably no more than 3 monomer units.

Suitably, the polymer is a co-polymer comprising first monomer unit residues bearing pendant carbohydrate or carbohydrate mimetic moieties and second monomer unit residues bearing pendant proximity based signal generating/modulating moieties. Alternatively or additionally, a single monomer unit residue bearing both pendant carbohydrate or carbohydrate mimetic moieties and pendant proximity based signal generating/modulating moieties may be used. The use of first and second monomer units is preferred, since the amounts of carbohydrate or carbohydrate mimetic moieties and proximity based signal generating/modulating moieties can then be controlled independently.

Preferably, the single monomer unit residues where present each bear both pendant carbohydrate or carbohydrate mimetic moieties and pendant proximity based signal generating/modulating moieties, and the first monomer unit residues and second monomer unit residues where present each bear pendant carbohydrate or carbohydrate mimetic moieties and pendant proximity based signal generating/modulating moieties respectively.

Preferably, the first monomer unit residues and second monomer units residues are different in structure not just in that they bear different pendant groups as explained above.

Preferably, the co-polymer is a random co-polymer. However, it may also be an alternating co-polymer. Use of a block co-polymer with large blocks is not preferred. However, a block co-polymer with blocks of low molecular weight (for example 1 to 3 kDa) may be used.

Preferably, when used in an assay with MBL as a carbohydrate binding molecule, the polymer binds to MBL at 0 mM glucose at least 50% as strongly as aminodextran, more preferably at least as strongly as aminodextran, but is more easily inhibited. It is particularly desirable that the polymer is easily inhibited (large proportion of total phase response) over the range of 0 to 35 mM glucose, and especially over the range of 2 to 15 mM. This provides an assay over glucose concentrations of particular physiological interest which is more sensitive than a similar assay using aminodextran as a glucose analogue.

More than one type of monomer unit residue bearing carbohydrate or carbohydrate mimetic moieties may be present. The carbohydrate or carbohydrate mimetic moieties may be different, with different affinities for MBL and similar lectins.

Similarly, more than one type of monomer unit residue bearing proximity based signal generating/modulating moieties may be used. The proximity based signal generating/modulating moieties may be different.

It is not necessary for the first monomer units (or single monomer units) to contain double bonds.

Examples of suitable carbohydrate moieties for use in such polymers are monosaccharides and oligosaccharides.

Preferably, the carbohydrate moieties have a high affinity for lectins, in particular MBL and other human or humanised lectins, and/or the plant lectin Concanavalin A.

It has been found by the inventors that the affinity of common carbohydrate moieties for MBL is as follows: D-Mannose, N-acetyl-D-mannosamine, D-fructose, D-leucrose, erlose, N-acetyl-D-glucosamine, L-Fucose>myo-inositol, D-glucose, D-arabinose, D-palatinose, D-turanose, D-sorbitol, D-ribose, D-tagatose>D-lyxose>lactose, L-arabinose, D-galactose.

Preferably, the carbohydrate moieties are not galactose, which has a low affinity for MBL.

The affinity of common sugar moieties for Concanavalin A is as follows (Van Damme et al., Handbook of Plant Lectins: Properties and Biomedical Applications, Wiley & Sons, 1998, p. 142):

Mannose>Glucose>N-acetylglucosamine.

Suitable monosaccharides are optionally derivatised tetroses, pentoses, hexoses, heptoses or higher homologous aldoses or ketoses, for example optionally derivatised D-glucose, D-mannose, N-acetyl-D-glucosamine, L-fucose, D-fructose, D-tagatose or D-sorbitol.

Suitable oligomers may be linear or branched homooligomers or mixed oligomers, for example containing from 2 to 50 carbohydrate units.

Where the polymer is to be used with MBL as carbohydrate binding molecule, the preferred glycosylation is 1→6 or 1→2, as 1→3 and 1→4 glycosylation is expected to interrupt MBL binding. For example, nona(1→6)-α-glucose (dextran 1500 Da) is expected to have higher avidity for MBL than 1,3-β-D-glucoses (e.g. laminanarihexaose). Suitable oligosaccharides include pannose, maltose, maltotriose, isomaltotriose, D-leucrose, erlose, D-palatinose, D-turanose or 1 to 250 kDa dextran (preferably 1 to 40 kDa dextran, for example 1 kda, 1.5 kDa, 5 kDa, 6 kDa, 10 kDa, 12 kDa, 20 kDa, 25 kDa or 40 kDa dextran).

Where the polymer is to be used with Concanavalin A as a carbohydrate binding molecule, 1→6 glycosylation is expected to interrupt Concanavalin A binding via the C6-OH hydroxyl groups. Preferred carbohydrate moieties in this case include optionally derivatised mannose, maltose, isomaltose, glucose and sophorose (not galactose), in particular α-D-mannopyranosides (α-D-Manp), α-D-glucopyranosides (α-D-Glup) and α-D-N-acetyl-glucosamine pyranosides (α-D-GluNAcp).

Preferably, the polymer comprises at least one carbohydrate moiety selected from D-fructose, D-leucrose, N-acetyl-glucosamine, D-mannose, L-fucose, N-acetyl-mannosamine, D-arabinose, myo-inositol, D-tagatose, erlose, D-glucose, D-palatinose, D-turanose, D-ribose, D-sorbitol.

More preferably, the polymer comprises at least one glucose moiety and/or at least one N-acetyl glucosamine moiety and/or at least one mannose moiety, since these have a high affinity for MBL and other animal lectins. It is believed that these moieties bind to binding sites of the lectin via their C3 and C4 hydroxyl groups.

Examples of a synthetic branched saccharide are dendrimer "wedges" used to construct dendrimers (e.g. TRIS derived trisaccharide with an amine linker, shown below).

The term "carbohydrate mimetic" includes non-carbohydrate molecules which bind to sites which normally bind carbohydrate, for example non-carbohydrate molecules which are able to compete with glucose to bind to MBL. Suitable carbohydrate mimetic moieties include peptides such as keratin peptide (SFGSGFGGGY) which mimics N-acetyl glucosamine. It has been shown that keratin peptide can inhibit MBL (Mantacto et al. 2001 J. Immunol. 166, 4148-4153).

Suitably, the first monomer units (or single monomer units) are each a double bond-containing derivative of a carbohydrate or carbohydrate mimetic moiety. However, the first monomer units (or single monomer units) may each be a double bond-containing molecule containing a functional group to which the carbohydrate or carbohydrate mimetic moiety can be linked, suitably after polymerisation.

Preferably, the double bond-containing derivative of the carbohydrate or carbohydrate mimetic moiety is an allyl or vinyl containing derivative of a carbohydrate or carbohydrate mimetic moiety. Other suitable double bond-containing derivatives of carbohydrate or carbohydrate mimetic moieties include homologues of allyl derivatives, for example 3-butenyl or 4-pentenyl derivatives, or styrene derivatives with the carbohydrate or carbohydrate mimetic moiety at the 4 position. Further suitable double bond-containing derivatives of carbohydrate or carbohydrate mimetic moieties include HEA, 2-hydroxyethyl methacrylate (HEMA) or vinyl alcohol (VA) based derivatives.

The carbohydrate or carbohydrate mimetic moieties may be linked to amine, acid, alcohol alkyne, azide, and/or sulphone functional groups of the first monomer units (or single monomer units). For example, alcohol groups in the monomer units and amine groups in the carbohydrate or carbohydrate mimetic moieties may be linked using divinylsulphone. Where the carbohydrate is mannose, the linkage is preferably not via the C3-OH or C4-OH groups, since these are important in binding to MBL. In this case, divinylsulphone linkage may be inappropriate.

Amino derivatised carbohydrate moieties can be produced by reductive amination of disaccharides. This allows the carbohydrate moiety to be linked at its anomeric position (C1).

The carbohydrate or carbohydrate mimetic moiety could be connected to alcohol groups (e.g. in HEA) by Fischer glycosidation.

In preferred embodiments, the first monomer units are each 1-allyl-α-D-mannopyranoside, 1-allyl-2-acetamido-2-deoxy-α-D-glucopyranoside and/or 1-allyl-α-D-glucopyranoside.

Suitably, the second monomer units (or single monomer units) are each a double bond-containing molecule containing a functional group to which the proximity based signal generating/modulating moiety can be linked, suitably after polymerisation. Suitable functional groups include acid, alcohol and/or sulphone. Linkage after polymerization helps to minimize loss of the expensive proximity based signal generating/modulating moieties.

However, the second monomer units (or single monomer units) may contain the proximity based signal generating/modulating moieties. In this case, the discussion above of suitable polymerisable groups and linkages applies.

In a preferred embodiment, the second monomer units are each N-(3-aminopropyl)methacrylamide or a derivative thereof.

In a preferred embodiment, the single monomer units are each a double bond containing, carbohydrate or carbohydrate mimetic moiety containing derivative of lysine. An example is shown below (multistep reaction scheme):

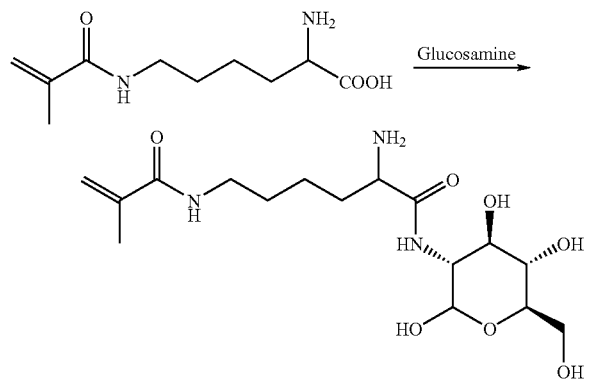

The starting material in this reaction scheme is methacryloyl-L-lysine, available through PolySciences Europe (Eppelheim, Germany). After polymerization, the alpha amine group could be linked to the proximity based signal generating/modulating moiety.

Preferably, the polymer further contains third monomer unit residues which do not bear pendant carbohydrate or carbohydrate mimetic or proximity based signal generating/modulating moieties. This helps to increase flexibility.

Preferably, the third monomer unit residues are different in structure from the single monomer unit residues, first monomer unit residues and/or second monomer unit residues (not just in that they bear different pendant groups as explained above).

Flexibility is increased by using third monomer units which are sterically unhindered such as HEA. Flexibility is also increased by using third monomer units which are uncharged. A polymer containing no third monomer units would have a large number of positively charged ammonium groups which would need to be inactivated to minimize decreased flexibility because of electrostatic repulsion. Third monomer units can be used to alter the overall charge of the polymer.

More than one type of third monomer can be included in the polymer.

Preferably, the third monomers units are each a double bond-containing molecule containing a hydrophilic group, for example a hydroxyl group. It is not preferred for the third monomers units to be a lipophilic double bond-containing molecule, for example styrene.

In a preferred embodiment, the third monomer units are each HEA, vinyl pyrrolidone, MMA, HEMA, vinyl alcohol and/or ethylene glycol. However, the skilled person will appreciate that there are many other double bond-containing molecules containing hydrophilic groups which could be used.

Suitably, the monomer units are reacted by addition polymerization. The addition polymerization may be free-radical initiated, for example using potassium peroxodisulfate (PPS) or another peroxide compound.

The polymerization method may be emulsion polymerization (discussed in U.S. Pat. No. 4,952,656), for example in a mixture of toluene and water. Suitably, surfactant is included in the emulsion polymerization reaction mixture. Surfactant can be removed after polymerization by de-emulsification and dialysis. Alternatively, the polymerization may be carried out in a single phase, for example in water.

Emulsion polymerization is believed to lead to a polymer with a lower average molecular weight and a narrower molecular weight distribution compared with single phase polymerization.

Suitably, the monomer units are mixed before initiator is added.

Preferably, the polymerization reaction takes less than two days. The length of the polymerization can be used to control the molecular weight of the polymer product.

Suitably, the polymerization reaction takes place under oxygen-free conditions, for example under a nitrogen atmosphere.

Suitably, the polymerization reaction is carried out at a temperature between 0° C. and 100° C., for example at room temperature or at 60° C.

Other possibilities are condensation polymerization (for example ionic condensation polymerization), ring opening polymerization and atom transfer radical polymerization (ATRP). The skilled person will appreciate that the nature of the monomer units will depend on the desired method of polymerization (for example double bond containing monomer units are not necessary for condensation polymerization).

Where no single monomer units are used, the first monomer units may be present in the reaction mixture in an amount of 20 to 70 mol % (or 20 to 70 wt %), for example in an amount of 30 to 50 mol % (or 30 to 50 wt %). Preferably, however, the first monomer units are present in the reaction mixture in an amount of 70 mol % to 90 mol %, more preferably in an amount of 75 mol % to 85 mol %, for example in an amount of 80 mol %. It has been found that using such an amount of first monomer units improves stability of the polymer solution. The stability problems experienced by the inventors related to solubility, seen in a tendency of the polymer to precipitate and a tendency not to dissolve after drying.

The second monomer units are preferably present in the reaction mixture in an amount of 5 to 15 mol % (or 5 to 15 wt %).

Where third monomer units are used, they are preferably present in the reaction mixture in an amount to make up the balance, for example 0 to 80 mol % (or 0 to 80 wt %).

It will be appreciated that the composition of the polymer does not exactly reflect the amounts of monomer units present in the reaction mixture. This is because of the influence of other factors (for example steric hindrance and solubility).

Suitably, the polymer carbohydrate content is in the range of 10 to 20 wt %. Preferably, however, the polymer carbohydrate content is in the range of 40 to 50 wt %. (These ranges are suitable for mannose in particular, and a higher carbohydrate content might be suitable for glucose). The polymer carbohydrate content can be determined as set out in Example A7 for certain carbohydrates (including mannose, glucose, galactose, xylose, fucose and galacturonic acid) but not others (including N-acetyl glucosamine and N-acetyl neuraminic acid).

It should also be noted that the carbohydrate analogue may consist of two or more separate entities which together act as a carbohydrate analogue. In particular, the carbohydrate analogue may consist of a first entity with at least two carbohydrate analogue moieties and a second entity which is a carbohydrate binding molecule such as a lectin. For example, acceptor labelled MBL and donor labelled MBL can be used together with unlabelled synthetic polymer as a template to bring the donor labelled MBL and acceptor labelled MBL in proximity of each other so that FRET occurs (example using Con A given by Gestwicki et al. (2002) *Chemistry and Biology* 9, p 163). (Similarly, acceptor labelled polymer and donor labelled polymer could be used with unlabelled carbohydrate binding molecule.)

Preferably, the carbohydrate analogue comprises one or more energy acceptor moieties (for example HMCV-1 or Alexa Fluor 594™, discussed below). However, it may also comprise one or more energy donor moieties.

The proximity based signal generating/modulating moieties may be attached to the carbohydrate analogue as discussed in connection with the carbohydrate or carbohydrate mimetic moieties above.

In a preferred embodiment, an activated carboxylic acid derivative (for example an active ester such as a succinimidyl ester), suitably linked to the proximity based signal generating/modulating moiety, is reacted with a nucleophilic group (for example an amine), suitably linked to the monomer unit or polymer. Such a reaction may be conducted in a polar aprotic solvent (for example DMSO). Suitably the reaction temperature is in the range of 0° C. to 100° C., for example room temperature.

An alternative method of attaching the proximity based signal generating/modulating moieties is to use Huisgen 1.3 dipolar cycloaddition between an azide group and an alkyne group (as developed by B. Sharpless).

The carbohydrate analogue should have a molecular weight high enough to prevent escape from the sensor but low enough that precipitation does not occur when the carbohydrate analogue binds to the carbohydrate binding molecule.

Carbohydrate analogues having an average molecular weight in the range of 25 to 250 kDa, more preferably 100 to 250 kDa, for example 150 kDa are preferred.

Optionally, the carbohydrate analogue and carbohydrate binding molecule are tethered together.

Carbohydrate Binding Molecule

Preferably, the carbohydrate binding molecule provides a stable signal in the assay for at least 10 days, more preferably for at least 14 days. It is particularly preferable that a stable signal be provided when the sensor is implanted in the human body.

Preferably, the carbohydrate binding molecule is a lectin, more preferably an animal lectin. However, it may also be another type of carbohydrate binding molecule, for example an antibody, or a plant lectin, for example Concanavalin A.

Preferably, the lectin is a C-type (calcium dependent) lectin.

Preferably, the animal lectin is a vertebrate lectin, for example a mammalian lectin, more preferably a human or humanized lectin. However, it may alternatively be a bird lectin, fish lectin or an invertebrate lectin such as an insect lectin.

Suitably, the lectin is a human lectin derived from the human body. Alternatively, the lectin may be a recombinantly manufactured lectin.

As a further alternative, the lectin may be a humanised animal lectin, for example a humanised bovine lectin. This applies where there is a corresponding human lectin. The lectin may be humanised in an analogous way to antibodies.

Suitably, the lectin is in multimeric form. Multimeric lectins may be derived from the human or animal body. Alternatively, the lectin may be in monomeric form. Monomeric lectins may be formed by recombinant methods or by disrupting the binding between sub-units in a natural multimeric lectin derived from the human or animal body. Examples of this are described in U.S. Pat. No. 6,232,130.

Preferably, the lectin has three or more CRDs. More preferably, the lectin has 6 or more CRDs.

Preferably, the lectin is a collectin (collagen-like lectin). These are C-type animal lectins which have collagen like sequences (Gly-Xaa-Yaa triplet). MBL is a C-type collectin whereas Concanavalin A is a C-type lectin. Monomeric collectin CRDs can be prepared by the action of collagenase.

Preferably, the lectin is mannose binding lectin, conglutinin or collectin-43 (e.g. bovine CL-43) (all serum collecting) or a pulmonary surfactant protein (lung collectins).

Suitably, the lectin is MBL substantially in trimeric and/or tetrameric form.

Alternatively, the lectin may be a pulmonary surfactant protein selected from SP-A and SP-D. These proteins are similar to MBL.

Other suitable animal lectins are those set out in the following list:
PC-lectin (US 20030216300, US 20040265898)
CTL-1 (US 179528/10)
Keratinocyte membrane lectins (Parfuemerie und Kosmetik 74, 164-80)
CD94 (Eur J Immunol 25, 2433-7)

P35 (synonym: human L-ficolin, a group of lectins) (Immunol Lett 67, 109-12)
ERGIC-53 (synonym: MR60) (Mol Biol Cell, 7, 483-93)
HIP/PAP (Eur J Biochem 267, 1665-71)
CLECSF8 (Eur J Immunol 34, 210-20)
DCL (group of lectins) (Appl no 00231996/US)
GLUT family proteins, especially GLUT1, GLUT4 and GLUT11 (PNAS 97, 1125-30)
Further suitable animal lectins are set out in Appendices A, B and C of "Handbook of Animal Lectins: Properties and Biomedical Applications", David C. Kilpatrick, Wiley 2000.
Preferably, the carbohydrate binding molecule is labelled with an energy donor moiety.

Detection

Suitable detection techniques include FRET, fluorescence energy transfer, fluorescence polarisation, fluorescence quenching, phosphorescence, luminescence enhancement, luminescence quenching, diffraction or plasmon resonance.

The binding assay generating the optical signal should preferably be reversible such that a continuous monitoring of fluctuating levels of analyte can be achieved. This reversibility is a particular advantage of the use of a binding assay format in which the components of the assay are not consumed.

The detectable or measurable optical signal is generated using a proximity based signal generating/modulating moiety pair. A signal is generated or modulated when a first member of the pair is brought into close proximity with a second member of the pair.

Preferably, the proximity based signal generating/modulating moiety pair is an energy donor moiety and energy acceptor moiety pair. Energy donor moieties and energy acceptor moieties are also referred to as donor and acceptor chromophores respectively. An energy acceptor which does not emit fluorescence is referred to as a quenching moiety.

In this case, the carbohydrate binding molecule is labelled with one of an energy donor and energy acceptor moiety pair and the carbohydrate analogue is labelled with the other of the energy donor and energy acceptor moiety pair.

The most preferred embodiment of the sensor of the invention incorporates an assay which generates an optical readout using the technique of FRET discussed above.

Where the assay is to be used in vivo, it is desirable for donors to fluoresce at 550 to around 700 nm and for acceptors to absorb light at around 650 nm. This avoids overlap between the donor fluorescence and in vivo autofluorescence at lower wavelengths.

Alexa Fluor 594™ (e.g. as succinimidyl ester) is an energy donor moiety with a suitable emission spectrum for use in vivo. This dye absorbs at 594 nm and fluoresces at 620 nm.

The HMCV dyes described in WO05/059037 are suitable energy acceptor moieties for use in the invention. These dyes are stabilised carbenium ions. An example is Hexa-Methoxy-Crystal Violet succinimidyl ester (HMCV-1).

Alternatively, QSY 21™ may be used as an energy acceptor moiety with Alexa Fluor 594™ as an energy donor moiety.

Fluorescence lifetime or fluorescence intensity measurements may be made. Fluorescence lifetime may be measured by phase modulation techniques (discussed below).

In a preferred embodiment, the carbohydrate binding molecule is labelled with AlexaFluor 594 as energy donor moiety, the carbohydrate analogue is labelled with HMCV-1 as energy acceptor moiety, and fluorescence lifetime is measured by phase modulation techniques.

The material retaining the assay components preferably provides sufficient space for the energy donor and the energy acceptor moieties to separate when not bound to one another so that energy transfer can cease.

Sensor Construction

Preferably, the ratio of carbohydrate binding molecule to polymer is 1 to 15 (µM carbohydrate binding molecule)/(mg/ml polymer), with 10 (µM carbohydrate binding molecule)/(mg/ml polymer) being particularly preferred.

It has been found that where MBL is used as carbohydrate binding molecule the assay sensitivity increases with this ratio up to a ratio of 10 (µM MBL)/(mg/ml polymer).

Also, using a high ratio of carbohydrate binding molecule to polymer allows a greater number of signal modulating moieties to be included in the polymer (thus increasing phase shift and hence assay sensitivity) without compromising the overall intensity of the assay.

Preferably, the components of the assay are retained by a material which has a pore size that permits diffusion of analyte but not the assay components. However, this selectivity may be achieved in other ways, for example by using a material which allows diffusion of uncharged materials.

Preferably, the components of the assay are retained by a shell or matrix material. The carbohydrate analogue and/or carbohydrate binding molecule may be grafted onto this material. More preferably, the material is biodegradable as described in WO00/02048. Optionally, the sensor may comprise small particles retained by a shell of biodegradable material as described in WO03/006992.

In a preferred embodiment, the components of the assay are retained by a shell of biodegradable material encapsulating the assay components whilst allowing analyte to contact the assay components, and the biodegradable material comprises a co-polymer having hydrophobic and hydrophilic units, as described in WO2005/110207.

One or more assay component chambers may be present within the shell.

Preferably, the co-polymer is a random copolymer.

Preferably, the co-polymer has a permeability of at least $5.0 \times 10^{-10}$ cm$^2$/s.

The word "permeability" is used to refer to the overall permeability of analyte (glucose) through hydrated co-polymer which can be measured experimentally.

Preferably, once implanted in the body the co-polymer degrades over a period of one week to one year, for example 30 days. For a typical polymer thickness of 5 µm this corresponds to a degradation rate of 0.17 µm/day.

Preferably, for mobility of glucose, the biodegradable material has a molecular weight cut-off limit of no more than 25000 Da. More preferably, the biodegradable material has a molecular weight cut-off limit of no more than 10000 Da.

Preferably, the weight fraction of the hydrophobic units is from 10 to 90% of the co-polymer, more preferably from 10 to 50% of the co-polymer.

Preferably, the molecular weight of each hydrophilic unit is from 200 to 10000 Da, more preferably from 400 to 4000 Da.

Preferably, the hydrophilic units of the co-polymer each comprise an ester of polyethylene glycol and a diacid. As an alternative to polyethylene glycol, a mixed polymer of ethylene glycol and propylene glycol may be used, and/or the polyether backbone may be substituted with hydrophobic and/or hydrophilic groups. As a further alternative to polyethylene glycol, poly-tetrahydrofuran (poly-THF) may be used.

Preferably, the hydrophilic units comprise terephthalic acid and/or succinic acid as diacids. Other suitable diacids are oxalic acid, tartaric acid, phthalic acid, aspartic acid, malonic acid and oligomeric or polymeric diacids, for example poly (dimer acid-sebacic acid). In one preferred embodiment, the diacid is terephthalic acid only. In an alternative preferred embodiment, the molar ratio of terephthalic acid to succinic acid is 1:2 to 2:1, suitably 1:1.

Alternatively, the hydrophilic units of the co-polymer may comprise oligomers. Suitable oligomers are oligomers of hydroxyethylmethacrylate (HEMA), vinylpyrrolidone, vinyl alcohol, carbohydrates, ethylene oxide and/or 2-acrylamido-2-methyl propane sulfonic acid. Where the hydrophilic units comprise HEMA, biodegradable linkages (for example ester linkages such as terephthalate linkages) are provided within the polymer to increase biodegradability.

Preferably, the molecular weight of each hydrophobic unit is from 400 to 5000 Da.

Preferably, the hydrophobic units of the co-polymer comprise an ester of butane-1,4-diol and a diacid. As an alternative to butane-1,4-diol, pentane-1,5-diol or hexane-1,6-diol may be used.

Preferably, the hydrophobic units comprise terephthalic acid and/or succinic acid as diacids. In a preferred embodiment, the molar ratio of terephthalic acid to succinic acid is 1:2 to 2:1, suitably 1:1. Alternatively, the hydrophobic units comprise terephthalic acid only as diacid. Other suitable diacids are given above.

Alternatively, the hydrophobic units of the co-polymer can comprise oligomers of methylmethacrylate (MMA), polyurethane and/or amides (for example Nylon-6, oligo-N-tertiary butylacrylamide or oligo-N-isopropylacrylamide). Where the hydrophobic units comprise MMA, biodegradable linkages (for example ester linkages such as terephthalate linkages) are provided within the polymer to increase biodegradability.

Preferred polymers have the general formula aPEG(T/S)bPB(T/S)c where "a" denotes the molecular weight of the PEG chain, "b" the weight fraction of the PEG(T/S) (polyethylene glycol terephthalate/succinylate) in the resulting polymer and "c" the weight fraction of the PB(T/S) (polybutylene terephthalate/succinylate) in the resulting polymer. Examples of such polymers are 600PEGT80PBT20, 1000PEGT80PBT20, 2000PEGT80PBT20, 4000PEGT80PBT20, 1000PEGT50PBT50 and 1000PEG(T/S)60PB(T/S)40(T/S 50%). The polymers are biodegradable, have high glucose permeability and have molecular weight cut-off properties at around 25000 Da.

Some of these polymers are disclosed in U.S. Pat. No. 6,383,220 and EP1247522.

The envelope of co-polymer preferably has a thickness of 1 to 50 μm.

In a third aspect, the present invention relates to a method of preparing a sensor as described herein.

Chemical methods for the preparation of polymer microcapsules include phase separation (coacervation), solvent evaporation and/or extraction.

Suitable physical methods for the preparation of polymer microcapsules include spray drying, spray coating, spray chilling, rotary disk atomisation, fluid bed coating, coextrusion (for example stationary nozzle coextrusion, centrifugal head coextrusion, or submerged nozzle coextrusion) and pan coating.

Sensor Use

In a fourth aspect, the present invention relates to a method of detecting a carbohydrate analyte using a sensor as described herein, comprising implantation of the sensor into the skin of a mammal, detection or measurement of carbohydrate analyte using external optical means.

In a fifth aspect, the present invention relates to a method of detecting a carbohydrate analyte using a sensor as claimed described above, comprising detection or measurement of carbohydrate analyte using external optical means by illumination of a said sensor present in or below the skin of a mammal.

Preferably, the method further comprises degradation of biodegradable material in the sensor.

The sensor may be introduced within the skin by injection, preferably using a syringe, or by other methods, in particular by any method described in WO00/02048. The sensor is preferably of a size suitable for injection through a narrow gauge needle to minimise the discomfort to the patient. Preferably, the sensor has a maximum dimension of 20 μm to 1 mm. However, a rod-shaped sensor having a larger maximum dimension may be used.

The sensor may be introduced within the thickness of the dermis, or subdermally, or may be introduced to the epidermis, although in the latter case it would be likely to be expelled from the skin by outgrowth of the epidermal layers, possibly before the biodegradable material has degraded.

Because the sensor is located within the skin, an optical signal generated in the sensor is preferably detected transcutaneously (i.e. through the higher layer(s) of the skin) thus obviating the need for any direct connection between the sensor and the external environment which may lead to infection.

However, detection may alternatively take place via a hollow or transparent means (for example a needle or optical fibre) which allows the sensor to be illuminated by external optical means without passing light through the skin.

Once the sensor is in place in a cutaneous location analyte measurements can be taken as often as is necessary with no adverse effects. This is a particular advantage in relation to the long-term care of diabetic patients because if glucose measurements are taken more frequently, tighter control can be maintained over the level of glucose in the blood and the risk of developing conditions related to poorly regulated blood glucose, such as retinopathy, nephropathy, neuropathy, general micro- and macrovascular damage and poor circulation, will be reduced.

Because the sensor of the invention does not itself contain any of the optical components required to interrogate the readout of the assay (these being preferably provided separately and located outside the body) the sensor can easily be provided in a form which is injectable with minimal discomfort to the patient.

Sensors incorporating an assay employing the technique of FRET may be interrogated by supplying incident radiation at a wavelength within the absorption spectrum of the energy donor moiety and measuring the intensity of the emitted fluorescence or the lifetime of the excited state. Commonly known methods are:
 1. Steady state measurement
 2 Time-domain lifetime measurement
   a. Single photon counting
   b. Streak camera
   c. Gated detection (pulse sampling)
   d. Up-conversion
 3. Frequency domain lifetime measurement
   a. Phase-modulation fluorometry (heterodyne detection)
   b. Phase sensitive detection (homodyne detection)

Further description of the principles may be found in Lakowicz, J. R. "Principles of Fluorescence Spectroscopy, Second Edition", 1999.

The preferred method for interrogating the assay is phase-modulation fluorometry.

A suitable optical set-up for interrogating the assay (FIG. 1) consists of a light-emitting diode (LED) 11, which emits light within the emission spectrum of the energy donor moiety. The LED is operated by a driver circuit 13, which modulates the LED at a frequency which results in a sufficient phase shift, preferably in the range of 45°. For a fluorophore with a lifetime of 3 ns, the preferred frequency is 50 MHz. The light emitted by the LED is filtered by an excitation filter 15 and directed towards the sensor 16 by a dichroic beam splitter 17 and focused onto the sensor/skin above the injected sensor 16 by a lens 19. The fluorescence emitted by the sensor is collected by the lens 19. The light passes through the dichroic beam splitter and is filtered through an emission filter 21. The filtered light is focused by a lens 23 onto the detector 25, in this case an avalanche photodiode (APD). The APD is reverse biased by an APD bias supply 27, which is controlled by a signal processing and control unit 29. The signal from the APD is amplified by a trans-impedance amplifier 31, filtered by a bandpass filter 33 and sampled by a first analog-to-digital converter (ADC) 35. Correspondingly, the modulated drive signal to the LED is sampled by a second ADC 37. The signal sampled on the first ADC 35 is:

$$Y_1(t) = A_1 * \sin(2*\pi*f*t + \phi_{f1} + \phi_1)$$

$A_1$ is the amplitude of the detected signal from the assay, f is the modulation frequency, $\phi_{f1}$ is the phase lag introduced by the donor fluorophore and $\phi_1$ is a fixed phase lag introduced by the electronic and optical set-up.

The signal sampled on the second ADC 37 is:

$$Y2(t) = A_2 * \sin(2*\pi*f*t + \phi_2)$$

$A_2$ is the amplitude of the modulated drive signal to the LED and $\phi_2$ is a fixed phase lag introduced by the electronic set-up The signal processing and control unit derives the phase lag $\phi_{f1}$ introduced by the energy donor moiety by comparing the two sampled signals and compensating for the fixed and known phase lags introduced by the electronics and optics.

Measurements are taken by holding the fluorometer close to the skin and in alignment with the sensor. The phase lag is converted to analyte concentration by the use of a phase-to-analyte-calibration function, such as $$\text{analyte concentration} = A + Bx/(k+x),$$

where A is the phase at no analyte present, B is the phase at maximal response, x is the measured phase, and k is the dissociation constant between the receptor and the analyte analogue.

An alternative measurement technique is measurement of fluorescence intensity.

In this case, the optical means should supply a first beam of incident radiation at a wavelength within the absorption spectrum of the energy donor moiety and preferably a second beam of incident radiation at a wavelength within the absorption spectrum of the energy acceptor moiety (this applies where the energy acceptor moiety is also a fluorophore). In addition, the optical means should preferably be capable of measuring optical signals generated in the sensor at two different wavelengths; wavelength 1 within the emission spectrum of the energy donor moiety (the signal generated in connection with the measurement of analyte) and wavelength 2 in the emission spectrum of the energy acceptor moiety (which could be the analyte signal or the internal reference or calibration signal).

The fluorometer separately measures the following parameters:

At Wavelength 1 (Energy Donor Moiety)
Excitation light intensity, I(1,0)
Ambient light intensity, I(1,1)
Intensity of combined fluorescent and ambient light, I(1,2)
At Wavelength 2 (Energy Acceptor Moiety)
Excitation light intensity, I(2,0)
Ambient light intensity, I(2,1)
Intensity of combined fluorescent and ambient light, I(2,2)

Again, measurements are taken by holding the fluorometer close to the skin and in alignment with the sensor. When making transcutaneous measurements of the fluorescent signals generated in the sensor it is necessary to take account of the absorption of signal by the skin. The absorptivity of human skin is found by experiment to be lowest in the range from 400 nm to 900 nm. The final output provided is the normalised ratio between the fluorescent intensity from the two fluorophores, defined by the following relation (Equation 1):

$$\text{Final output} = (I(1,2) - I(1,1)) * I(2,0) / (I(2,2) - I(2,1)) * I(1,0) \qquad (1)$$

The final output from the optical means (e.g. the fluorometer) as given by Equation 1 above is converted to analyte concentration preferably by means of a computer using calibration data which can be obtained based on the principles set out in WO00/02048.

FURTHER ASPECTS OF INVENTION

In a sixth aspect, the invention relates to a polymer as described above.

Features described in connection with any aspect of the invention can be applied to other aspects of the invention.

The invention will be further illustrated with reference to examples, and to the Figures in which:

FIG. 4a shows the FRET assay results obtained in Example A9a.

EXAMPLES

General

Figure 1:
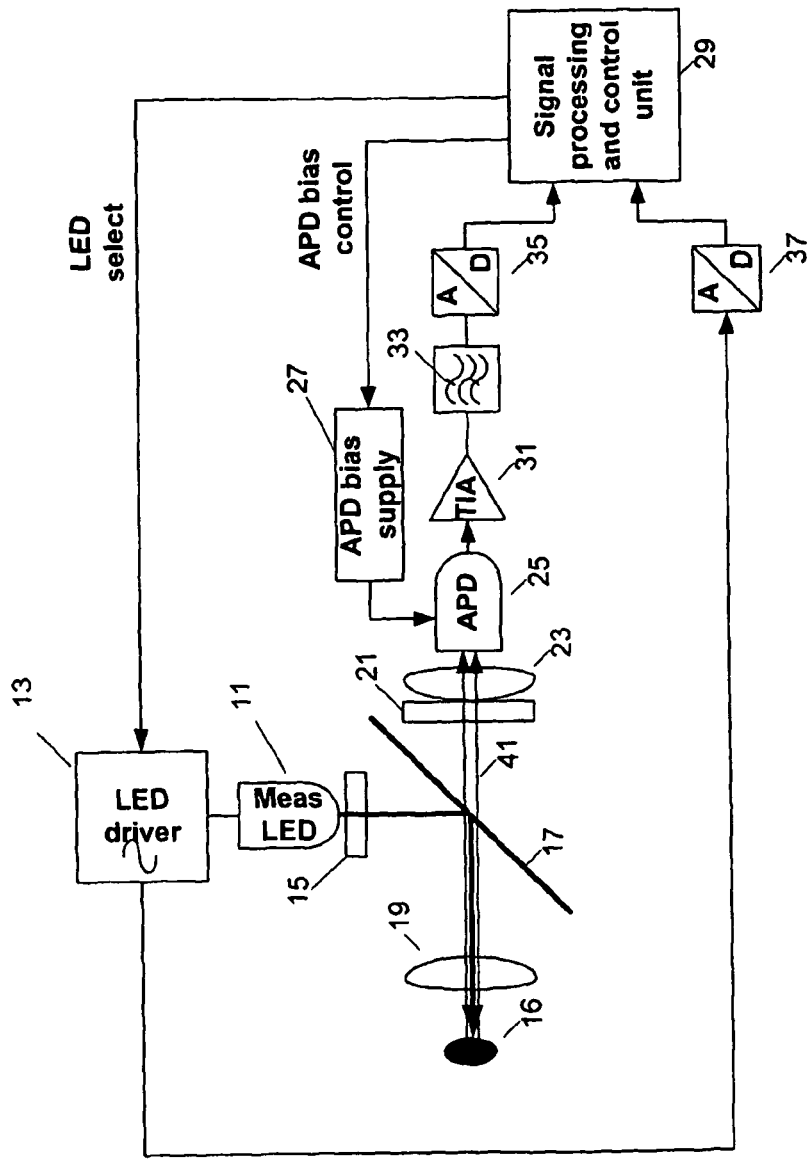
FIG. 1 shows a suitable optical set-up for interrogating the assay.

The following materials were used:

Sodium periodate, Biotin-N-hydroxy succinimide, o-phenylene dihydrochloride, benzylamine, ammonia, sodium cyanoborohydride (Sigma-Aldrich).

Nunc F96 MaxiSorp plate (Nunc, Denmark).

PD-10 columns, Streptavidin-HRP (Amersham bioscience).

Dextrans (Pharmacosmos, Denmark).

Mannan binding lectin (available from several sources e.g. Statens Serum Institute, Copenhagen, Denmark). Concanavalin A peroxidase conjugate (Sigma-Aldrich, L6397).

Dialysis tube Spectra/Por (Spectrum Laboratories Inc., California, USA). Float-A-Lyzer™ 25.000 MWCO regenerated cellulose dialysis tubing was from Spectrum Laboratories Europe (Breda, The Netherlands).

Sorbitan monooleate (Span® 80), Azodiisobutyrodinitrile (AIBN) and 2-hydroxyethylacrylate were from Sigma-Aldrich. N-(3-aminopropyl)methacrylamide hydrochloride was from PolySciences Europe (Eppelheim, Germany). 2,2'-Azobis[2-(2-imidazolin-2-yl)propane]dihydrochloride (VA-044) was from Wako GmbH (Neuss, Germany).

Allyl α-D-Glucopyranoside and Allyl 2-acetamido-2-deoxy-α-D-glucopyranoside were from Glycon Biochemicals, Germany. Allyl α-D-Galactopyranoside was from Sigma-Aldrich. Allyl α-D-mannopyranoside was prepared in house by the method of Example C1.

PBS is 20 mM Phosphate, 150 mM NaCl, pH 7.4, and TBS is 20 mM TRIS, 150 mM NaCl, 1.25 mM $CaCl_2$, pH 7.4 unless otherwise stated.

Abbreviations: MBL, Mannan Binding Lectin; PBS, Phosphate buffered saline; TBS, TRIS buffered saline; ELLA, Enzyme Linked Lectin Assay.

Example A1

Staining of MBL

Human MBL was buffer changed (by dialysis) to a 10 mM $NaHCO_3$ buffer containing 150 mM NaCl and 1.25 mM $Ca^{2+}$, pH 8.7. The dye used for staining was Alexa Fluor™ 594 succinimidyl ester (AF594-SE) (Molecular Probes, Eugene, Oreg., USA). The dye was dissolved in dry DMSO and added slowly (10 min.) to the MBL in bicarbonate buffer. Reaction was allowed to take place for 1 hour. The staining was performed with 15 times molar excess (with respect to the polypeptide unit) of dye. Purification was carried out by dialysis against 10 mM Tris buffer pH 7.4, 150 mM NaCl and 1.25 mM $Ca^{2+}$. The obtained molar-based degree of labelling of the stained protein was determined by UV spectroscopy as 2.3 dyes per subunit of MBL (calculated using 28 kDa as molecular weight of MBL subunit).

Example A2

Preparation of Dextran 150 kDa Dextran (6.00 g, 0.4 μmol) was dissolved in 250 mM $K_2HPO_4$ pH 11.5 (600 mL). Sodium borohydride (3 g, 0.08 mol) was added followed by the addition of divinylsulfone (15 ml, 0.15 mol). The reaction mixture was stirred for 30 min at RT, before neutralization to pH 7.2 with conc. HCl. After 30 min stirring, the resulting mixture was dialysed (MWCO 10-12 kDa) in water (3×25 L). The contents were transferred to an Erlenmeyer flask and 24% ammonia (200 mL) was added. After 2 h, the pH was adjusted to 10.5, and the reaction was stirred overnight. Excess ammonia was removed by dialysis (MWCO 10-12 k) in water (8×25 L), and the entire contents were lyophilised to yield the aminodextran 5.75 g (78%, based on an aminodextran MW of 185 kDa) as a white fluffy substance. Elemental analysis was used to make a rough estimate of the molecular weight, amine incorporation, and amount of incorporated divinylsulfone. (Found C, 39.86; H, 6.26; N, 0.16; S, 3.08%. Dextran 150 k, ~22 DVS—$NH_2$, ~160 DVS-OH, and ~720$H_2O$ requires C, 39.55; H, 6.60; N, 0.16; S, 3.07%).

Example A3

Preparation of Hexa-Methoxy-Crystal Violet Succinimidyl Ester (HMCV-1)

Synthesis of HMCV-1:

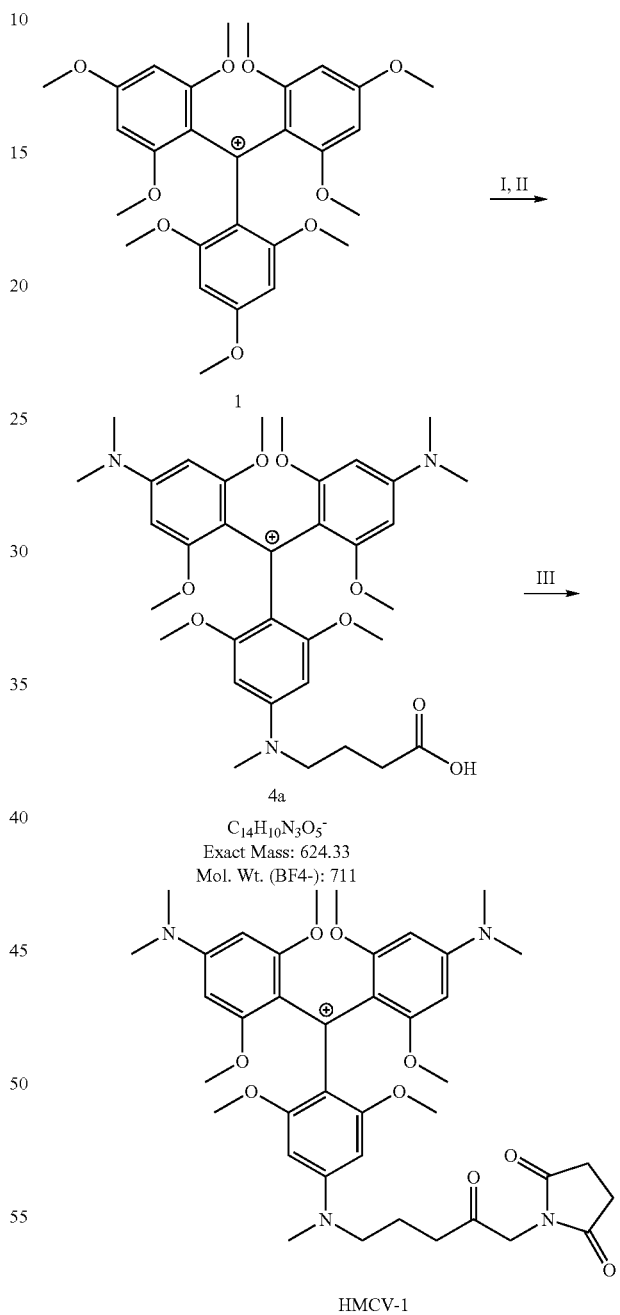

Scheme 1.

1
$C_{14}H_{10}N_3O_5^-$
Exact Mass: 624.33
Mol. Wt. (BF4-): 711

4a

HMCV-1
$C_{34}H_{17}N_2O_{10}^+$
Exact Mass: 721.34
Mol. Wt. (Cl-): 757

I) 4-(N-methylamino)-butanic acid hydrochloride (1 eq.), Diisopropylethylamine, in acetonitrile, 20° C., 20 hours. II) Dimethylamine (excess). III) TSTU, Diisopropylethylamine, in acetonitrile, 20° C., 2 hours.

4a ($BF_4^-$): 4-(methylamino)butyric acid hydrochloride (1.36 g; 8.8 mmol), 1 (5.0 g; 8.3 mmol), and diisopropylethylamine (5 mL) was dissolved in acetonitrile (120 mL). The reaction mixture was stirred at 30-35° C. in a dry nitrogen atmosphere for 22 h. Aqueous dimethylamine (40 mL of a 40% solution) was added and the reaction mixture was stirred for four more days. Solvent and excess dimethylamine were removed in vacuo and the remaining material dissolved in chloroform. The chloroform solution was washed twice with brine and dried over $MgSO_4$ before evaporation of the solvent and reprecipitation of the product from $CH_2Cl_2$/ether. Yield: 4.4 g (70%) of a dark blue powder.

MS (FAB+): m/z 624 (M+)

$^1$H-NMR (400 MHz, DMSO-$d_6$): δ 8.34 (1H, bs), 6.03 (2H, s), 5.83 (4H, s), 3.49 (2H, m), 3.46 (6H, s), 3.44 (12H, s), 3.12 (3H, s (masked)), 3.08 (12H, s), 1.94 (2H, t), 1.70 (2H, m).

HMCV-1 (Cl$^-$): TSTU (2-succinimido-1,1,3,3-tetramethyluronium tetrafluoroborate; 0.8 g, 2.6 mmol) was added to a solution of 4a (0.9 g, 1.26 mmol) and diisopropylethylamine (0.55 g, 4.5 mmol) in acetonitrile (15 mL). The reaction mixture was stirred in a closed flask for 2 h, before it was poured into an ice-cold nearly sat. NaCl solution (approx. 150 mL) acidified with HCl-aq (4 mL, 2 M). The water phase was extracted with chloroform (2×150 mL). The combined chloroform phases was washed with brine (2×50 mL) and dried over $MgSO_4$. Evaporation of the solvent and reprecipitation from $CH_2Cl_2$/ether gave a dark blue powder (0.80 g, 84%).

MS (FAB+): m/z 721 (M+)

$^1$H-NMR $^1$H-NMR br. (400 MHz, DMSO-$d_6$): δ 5.88 (2H, s), 5.85 (4H, s), 3.60 (2H, s), 3.46 (12H, s), 3.45 (6H, s), 3.15 (12H, s), 3.12 (3H, s), 2.85 (4H, s), 2.80 (2H, t), 1.95 (2H, m).

Example A4

40 mol % Mannose Polymer Synthesis

A 40 mol % mannose polymer was prepared as follows. Allyl α-D-mannopyranoside (1.77 g, 8.0 mmol), 2-hydroxyethylacrylate (1.36 g, 11.7 mmol), N-(3-aminopropyl)methacrylamide hydrochloride (89.6 mg, 0.5 mmol) and 2,2'-Azobis-[2-(2-imidazolin-2-yl)-propane]dihydrochloride (23.7 mg, 0.073 mmol) were added into a 50 ml round bottom flask, followed by addition of water (28.8 ml). The mixture was dissolved under magnetic stirring at room temperature. After purging with nitrogen for 5 min, the mixture was heated to 60° C. and polymerized at that temperature for 12 hours. Upon cooling a slightly yellow and viscous solution was obtained. This solution was dialysed (25 k MWCO regenerated cellulose) overnight against water, and freeze-dried to obtain a white fluffy polymer.

After this polymer had dried and been exposed to air it was only partially soluble in water.

Example A4a

80 mol % Mannose Polymer Synthesis

An 80 mol % mannose polymer was prepared as in Example A4, except that the amount of allyl-α-D-mannopyranoside was 3.54 g (16 mmol) and the amount of 2-hydroxyethylacrylate was 0.68 g (5.85 mmol).

This polymer was more soluble than the polymer prepared in Example A4. Also, after this polymer had dried and been exposed to air it was still soluble in water.

Example A5

Labelling 40 mol % Mannose Polymer of Example A4 with HMCV-1

The polymer of Example A4 (20 mg) was dissolved in 10 mM carbonate buffer (500 μl, pH 8.6) and a solution of hexamethoxycrystalviolet-succinimidyl ester (HMCV-1, 6.1 mg) prepared as in Example A3 in DMSO (200 μl) was added. The mixture was gently stirred for 3 hours at room temperature, and then dialysed (10 k MWCO regenerated cellulose) against 10 mM TBS buffer, pH 7.4 to remove unreacted dye. A weight-based degree of labelling ("DOL") value of 0.085 was obtained.

The "DOL" value was determined using the following equation

"DOL"=[HMCV-1](mg/ml)/(polymer)(mg/ml)

Where the HMCV-1 content was determined spectrophotometrically:

[HMCV-1](mg/ml)=[$A$(632 nm)/(ε(HMCV-1, 632 nm)*1)]*$M$(HMCV-1)

ε(HMCV-1, 632 nm)=42000 M$^{-1}$*cm$^{-1}$; M(HMCV-1)= 660.2 g/mol

Example A5a

Labelling 80 mol % Mannose Polymer of Example A4a with HMCV-1

The labelling method of Example A5 was carried out on the 80 mol % mannose polymer of Example A4a.

Example A6

Size-Exclusion Assay on 40 mol % Mannose Polymer of Example A4

Figure 2:
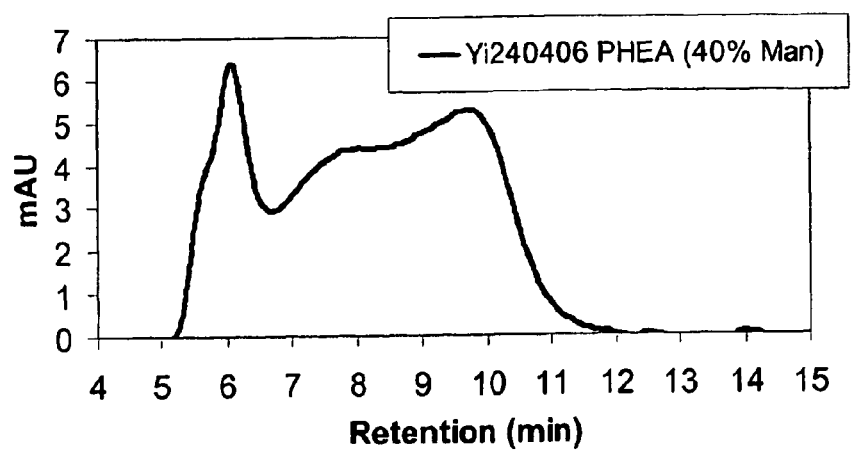
FIG. 2 shows the size exclusion chromatography results obtained in Example A5.
Figure 2:
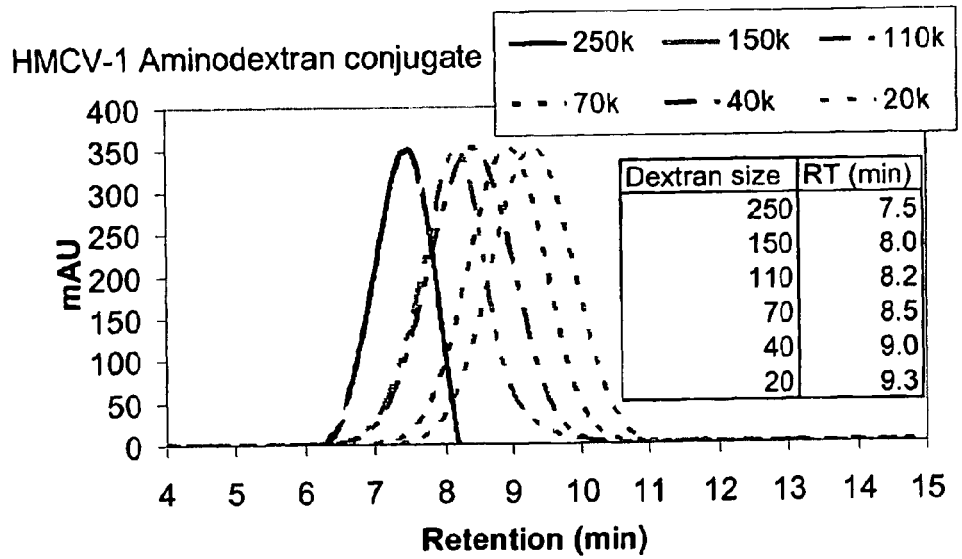

The molecular weight of the polymer of Example A4 was determined using size-exclusion chromatography. A TSKgel G4000PW$_{XL}$ column (7.8 mm ID×30.0 cm L, Tosoh Biosciences GmbH) was operated on an Agilent 1100 HPLC system. An isocratic elution (1.0 ml/min for 25 min) of the mobile phase (0.1% acetic acid, 50 mM NaCl, pH 3.4) was used. Molecular weight was based on HMCV conjugated aminodextran standards using the following relation: Mw=10^(6.7336−0.5755*RT). The results are shown in FIG. 2.

Example A7

Determination of Mannose Content of Polymer of Example A4

This assay is based on dehydration of mannose (in 80% sulphuric acid) to the corresponding 5-hydroxymethylfurfural (5-HMF) which is subsequently reacted with 5% phenol solution to produce a chromogen upon heating. Since this reaction is quantitative, the original concentration of mannose can be determined spectrophotometrically. Using a 96-well microplate allows for a high throughput of samples. The method used is modified from Masuko et al. (2005) *Anal. Biochem.*, 339, 69-72.

To 50 μl of sample in a well of a 96-well microplate was added 150 μl of concentrated sulphuric acid rapidly to cause maximum mixing, followed immediately by 30 μl of 5% phenol in water. After incubation for 15 minutes at 90° C. in a water bath by floating the microplate carefully, the plate was cooled for 5 minutes in another water bath and wiped dry to measure Abs (490 nm) using a microplate reader. The samples consisted of 12 different concentrations (0.003, 0.02, 0.03, 0.05, 0.15, 0.2, 0.3, 0.5, 1.0, 1.5, 2.0, 3.0 mM) of mannose in water (50 μl/well) to generate a standard curve, and three different concentrations (0.5, 1.0, 2.0 mg/ml) of the polymer of Example A4 (50 μl/well). All measurements were made with sample triplicates.

The results are shown in Table 1.

TABLE 1

YIH240406 PHEA 40% Man

| Polymer (mg/ml) | Abs (490) | Mannose (mM) | Mannose (mM) in 1 mg/ml | Weight % | Avg. Weight % |
|---|---|---|---|---|---|
| 2.0 | 1.533 | 1.95 | 0.97 | 21% | 17% |
| 1.0 | 0.559 | 0.69 | 0.69 | 15% | |
| 0.5 | 0.269 | 0.32 | 0.63 | 14% | |

Std. Curve: y = 0.7752x + 0.025 (R2 = 0.9988)

Example A7a

Determination of Mannose Content of Polymer of Example A4a

The polymer of Example A4a was analysed using the method described in Example A7.

The results are shown in Table 1a.

TABLE 1a

YIH140806-PHEA-Man 80%

| Polymer (mg/ml) | Abs (490) | Man (mM) | Man (mM) in 1 mg/ml | Weight % | Avg. Weight % |
|---|---|---|---|---|---|
| 1.0 | 1.622 | 1.87 | 1.870 | 41% | 41% |
| 0.5 | 0.831 | 0.95 | 1.896 | 42% | |
| 0.25 | 0.417 | 0.47 | 1.864 | 41% | |

Example A8

ELLA Assay on 40 mol % Mannose Polymer of Example A4

Biotinylated MBL was prepared as follows. Biotin-NHS (20 μl, 7 mg/ml in DMSO, ~10-15 eq. per MBL monomer) was added to a solution of MBL (3 ml, 0.53 mg) in PBS (3 mL). The solution was gently stirred for 2 h, then transferred to a dialysis tube (MWCO 10-12K) and dialysed against TBS (2×1 L) over the course of 24 h. The resulting biotinylated MBL (0.2 mg/ml) in TBS was used without further purification.

A standard ConA ELLA assay was performed as follows to confirm that the coating concentration used for the MBL ELLA assay described below was enough to saturate the microplate. PBS buffer used in the ELLA assay was 10 mM Phosphate, 150 mM NaCl, 0.1 mM $CaCl_2$, 0.1 mM $MnCl_2$, pH 7.4.

Figure 3:
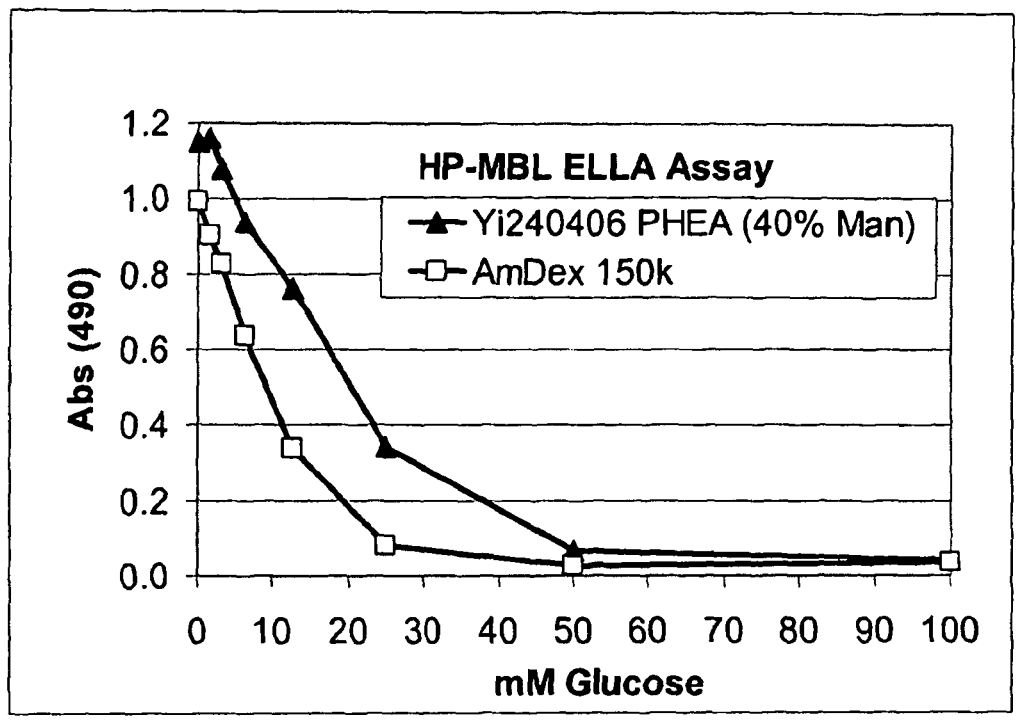
FIG. 3 shows the ELLA assay results obtained in Example A8.

A 96-well microtiter plate was coated, overnight at 5° C., with two columns of each of the antigens (polymer from Example A4 and aminodextran) (100 μl, 100 μg/ml, 2-fold dilutions) in PBS. Residual binding sites were blocked by the addition of 0.5% (w/v) BSA in PBS (150 μl). The wells were then washed (2×200 μl PBS). ConA-HRP 1% (w/v) (100 μl) in PBS was added and incubated for 1 h. Plates were then emptied and washed (3×200 μl PBS). The presence of HRP was visualized by the addition of substrate solution (1 mg o-phenylene dihydrochloride) and quenched after 2 min with 1 N $H_2SO_4$. Color development was determined by reading the absorbance at 490 nm, with background subtraction at 630 nm. A 96-well microtiter plate was coated, overnight at 5° C., with two columns of each of the antigens (polymer of Example A4 and aminodextran) (100 μl, 100 μg/ml) in TBS. Residual binding sites were blocked by the addition of 0.5% (w/v) BSA in TBS (150 μl). The wells were then washed (2×200 μl TBS). Dilutions of glucose (from 100 mM to 0 mM) in biotinylated MBL (2 μg/ml) were added to a total volume of 100 μl. After incubation for 2 h, the plate was emptied and washed (2×200 μl TBS). Streptavidin-HRP 0.1% (v/v) (100 μl) in TBS was added and incubated for 1 h. Plates were then emptied and washed (3×200 μl TBS). The presence of HRP was visualized by the addition of substrate solution (1 mg o-phenylen dihydrochloride) and quenched after 2 min with 1 N $H_2SO_4$. Color development was determined by reading the absorbance at 490 nm, with background subtraction at 630 nm. The results are shown in FIG. 3.

Example A8a

ELLA Assay on 80 mol % Mannose Polymer of Example A4a

An ELLA assay was conducted on the polymer of Example A4a using the method described in Example A8.

The IC50 value generated by the ELLA assay was much higher than that of Example A8. IC50 varied from 50-80 mM glucose, as compared with 16.8 mM glucose (A8).

Example A9

FRET Assay on 40 mol % Mannose Labelled Polymer of Example A5

Measurements were taken with the frequency-domain technique. For these measurements a KOALA instrument (KOALA automated sample compartment) from ISS Inc., Urbana, Ill., USA was used. The excitation light source (11 in FIG. 1) was a yellow LED. The excitation light was filtered through a 540 to 590 nm bandpass filter (15 in FIG. 1) and the emission was isolated using a 610 to 690 nm bandpass filter (21 in FIG. 1), both from Omega Optical Inc., Brattleboro, Vt., USA.

A multiexponential decay model best describes the fluorescence decay. However, for glucose sensing it is not necessary to resolve the multiexponential decays. Phase or modulation measurements at a single modulation frequency are adequate to determine the glucose concentration (L. Tolosa, H. Szmcinski, G. Rao and J. R. Lakowicz (1997) *Analytical Chemistry* 250, 102-108). It is believed that the optimal modulation-frequency for the PreciSense assay chemistry is 61 MHz.

50 μl of assay chemistry of 10 μM labelled MBL (prepared as in Example A1 but with a degree of labeling of 0.5 dyes per MBL subunit) and 2 mg/ml labelled polymer (Example A5) was mixed and allowed to stand for at least 1 h after mixing. The assay chemistry (5 μl) was then transferred to a cellulose fibre with a syringe and the fibre was mounted in a custom designed fibre-holder. The fibre-holder fitted into a standard fluorescence cell (10 mm×10 mm). Hence, a standard commercial instrument without modifications was used for the measurements.

All solutions were pre-heated to 34° C. in a water bath, and all measurements in the KOALA instrument were recorded at 34° C. The fluorescence cell containing the fibre and fibre-holder assembly was placed in the sample holder of the KOALA, and the fluorescence cell was filled with buffer containing glucose.

The measured phase was an average of at least forty phase-angle recordings. After the completion of a measurement, the fluorescence cell was emptied using a pipette, and refilled with buffer containing the next concentration of glucose. A delay of 20 minutes between measurements was used to allow the assay chemistry to reach equilibrium.

Figure 4:
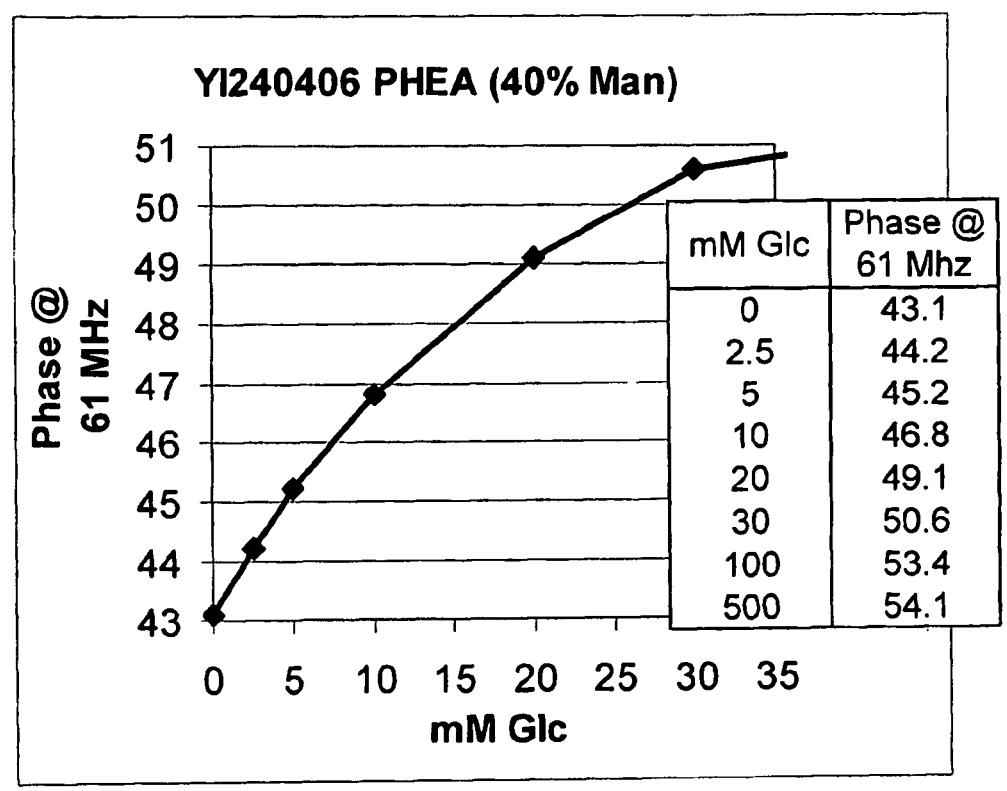
FIG. 4 shows the FRET assay results obtained in Example A9.

To generate a glucose dose-response curve (FIG. 4), the phase was measured at 0, 2.5, 5, 10, 30, 100 and 500 mM glucose. After determination of the phase-angle at 500 mM glucose the fibre was washed several times with 10 mM TRIS buffer over a time period of 60 minutes. At this point the same phase-angle was obtained as was initially obtained for 0 mM Glucose. This demonstrates the reversibility of the assay (data not shown).

Example A9a

FRET Assay on Labelled Polymers of Example A5 and A5a

A method similar to that of Example A9 was carried out using the labelled polymers of Examples A5 and A5a. Each polymer was encapsulated in a biodegradable polymer and measurements were taken with a miniaturised time resolved fluorometer. The glucose concentration was varied between 2.5 mM, 5 mM, 15 mM and 30 mM in cycles over 2 days. Measurements were taken at 5 minute intervals and the phase shift was calculated by subtracting the value of the phase measured at the first 2.5 mM glucose level from the subsequent phase values.

Figure 4A:
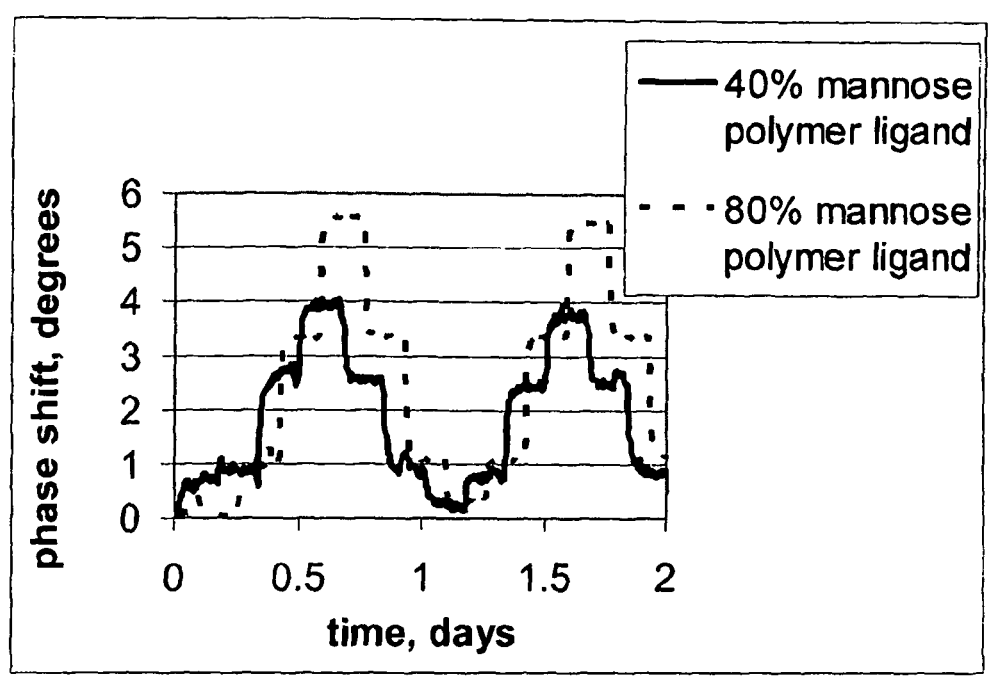

The results are shown in FIG. 4*a*.

The 80% mannose labelled polymer (Example A5a) had a phase shift approximately 40% larger than the 40% mannose labelled polymer (Example A5).

Precipitation of the 40 mol % mannose labelled polymer (Example A5) was observed. No precipitation of the 80% mannose labelled polymer (Example A5a) was observed. It is thought that this is connected to the improved response of the 80 mol % mannose labelled polymer.

The results of Examples A4 to A9 are summarized in Table 2.

TABLE 2

| FRET | Response from 0-30 mM Glc | Response from 0-500 mM Glc |
|---|---|---|
| Labelled polymer of Example A5 | 7.5° | 11.0° |
| SEC | Retention time | Estimated size (based on dextran standard) |
| Polymer of Example A4 | 6.1; 7.9; 9.7 | 150k (Mw range 6k → >3000k) |
| ELLA | ConA Affinity Abs(12.5 µg/ml) | MBL affinity (IC$_{50}$) or Abs(0 mM Glc) |
| Polymer of Example A4 AmDex 150k | 0.94 0.60 | 16.8 9.7 |
| Phenol-sulfuric acid assay | mM Carbohydrate (1.0 mg/ml Polymer) | Weight % |
| Polymer of Example A4 | 0.66 | 17% |

The results of Examples A4a to A9a are summarized in Table 2a.

TABLE 2a

| FRET | Response from 0-30 mM Glc | Response from 0-500 mM Glc |
|---|---|---|
| Labelled polymer of Example A5a | 7.5° | 11.6° |
| SEC | Retention time | Estimated size (based on dextran standard) |
| Polymer of Example A4 | N.A. | N.A. |
| ELLA | ConA Affinity Abs(12.5 µg/ml) | MBL affinity (IC$_{50}$) or Abs(0 mM Glc) |
| Polymer of Example A4a AmDex 150k | 1.0 0.60 | 50-80 9.7 |
| Phenol-sulfuric acid assay | mM Carbohydrate (1.0 mg/ml Polymer) | Weight % |
| Polymer of Example A4a | 1.59 | 41% |

Example A10

Sensor Formulation and Implantation

Fibres were made from 1000PEGT80PBT20 polymer (prepared as described in S. Fakirov and T. Gogeva, Macromol. Chem. 191 (1990) 603-614 with a target of 80 wt % hydrophilic segment and 20 wt % hydrophobic segment) by dipping a glass rod of diameter 700 µm into a 15% w/w solution of polymer in dichloromethane (DCM) and letting it dry at room temperature. This yielded hollow fibres of outer diameter 900 µm with a lumen of diameter 700 µm. The fibre was filled with assay chemistry (Example A9). Heating the polymer in order to melt it closed the fibre. The welded fibre was tested for leakage before testing and insertion.

This type of fibre can be placed in the top of the skin by the use of a needle. A needle of suitable size (large enough to contain the wet fibre) is placed parallel to the skin surface at a depth of approx. 1 mm leaving the needle visible as a shadow through the skin. The fibre (still wet) is placed inside the needle and the needle is removed. Typically no bleeding is observed at the insertion site after the insertion procedure is completed.

When the fibre is in place the reading device is placed directly above the fibre and the measurements can begin.

Example B1

Polymer Synthesis

A water-soluble 40 mol % Mannose copolymer was prepared by emulsion polymerisation as follows.

To a 250 ml three-necked round-bottomed flask equipped with a mechanical stirrer and a nitrogen tube was added Span80 surfactant (5.7 g; HLB [hydrophile lipophile balance] 4.3, 10% w/w based on toluene), AIBN (30 mg) and toluene (57.3 g). The flask was sealed, purged with nitrogen, and kept under a nitrogen atmosphere throughout the polymerisation. Allyl α-D-Mannopyranoside (3.52 g), 2-hydroxyethylacrylate (2.552 g), and N-(3-aminopropyl) methacrylamide hydrochloride (0.356 g) were dissolved in water (12.7 g) and filtered to remove insoluble material. This mixture was added to the vigorously stirred mixture in the round-bottomed flask through a rubber septum.

The reaction mixture was stirred at room temperature until a stable emulsion was formed (30 min), then at 60° C. for 4 h. A solution of VA-044 (1 ml, 60 mg/ml) was injected through the septum and polymerisation was continued overnight (17 h). The reaction mixture was cooled to room temperature and the emulsion was disrupted by the addition of acetone. This caused precipitation of the polymer, which was collected, redissolved in water, and precipitated by addition of acetone. The product was dried overnight under vacuum to yield 3.2 g (50%) crude light yellow polymer. Part of the crude polymer (1.0 g) was dissolved in water (10 ml), and dialysed (MWCO [molecular weight cut off] 25,000) in water to remove low molecular weight material. Freeze-drying yielded 0.46 g (46%) fluffy white polymer.

Example B2

Staining of Polymer of Example B1

In general the labelling of the polymer follows the description provided by Molecular Probes (product information MP00143, Rev. June 2001).

The polymer (Example B1) (88.6 mg) was dissolved in 10 mM NaHCO$_3$ solution (3 ml; pH 8.5). The polymer solution was divided equally into three Eppendorf vials. HMCV-1 (Example A3) (19.6 mg; 26.1 µmol) was dissolved in dry DMSO (600 µl). The dye was added to the polymer solutions in 10 µl aliquots every 30 seconds, in such a manner that the first vial in total received 100 µl, the second vial received 200 µl and the third vial received 300 µl. After the addition of the last aliquot, the vials were gently stirred for one hour before the solutions were dialysed (MWCO 10-12,000) in 10 mM TRIS buffer with several buffer changes and until no colour was visible in the dialysis buffer (usually 6-8 buffer changes of 500 ml and 72 hours).

Example B3

FRET assay on Polymer of Example B2

Assay chemistry including stained polymer solution (Example B2) (4 µL) and stained MBL solution (Example A1) (8.5 µL) in 10 mM TRIS buffer (12.5 µL) was mixed and allowed to stand for at least 1 h after mixing. The assay chemistry was then transferred to a fibre as in Example A9 with a syringe. The fibre was mounted in a custom designed fibre-holder which fitted into a standard fluorescence cell (10 mm×10 mm). The glucose response was measured by the use of time resolved fluorescence spectroscopy (frequency domain).

Example C1

Synthesis of Allyl α-D-Mannopyranoside and Aminodextran 150k

Synthesis of allyl α-D-Mannopyranoside was carried out essentially as described in Pekari et al. (2004) *J. Org. Chem,* 66(22), 7432-7442.

D-Mannose (12.1 g, 67 mmol) was refluxed overnight in dry allyl alcohol (140 ml) in the presence of BF$_3$—OEt$_2$ (0.58 ml). The reaction mixture was neutralised with Et$_3$N (1.8 ml) the following day, and the solvent evaporated. Dry Column Vacuum Chromatography (id 6 cm; 100 ml fractions; 0-45% MeOH in DCM (v/v)—11 fractions, 5% increments+100%) afforded the product 9.38 g (63%) as a colourless syrup. TLC (DCM-MeOH, 9:1) R$_f$ 0.3; $^1$H-NMR (300 MHz, 128 scans, 4 mg in 700 µl D$_2$O) δ 3.27 (s, 2H, Allyl), 3.52-4.21 (m, 6H), 4.84 (bs, 1H, αH), 5.16-5.34 (m, 2H, Allyl), 5.82-5.98 (m, 1H, Allyl).

Synthesis of aminodextran 150 k was carried out as follows. Dextran 150k (6.00 g, 0.4 µmol) was dissolved in 250 mM K$_2$HPO$_4$ pH 11.5 (600 mL). Sodium borohydride (3 g, 0.08 mol) was added followed by the addition of divinylsulfone (15 ml, 0.15 mol). The reaction was stirred for 30 min at RT, before neutralization to pH 7.2 with conc. HCl. After 30 min stirring, the resulting mixture was dialyzed (MWCO 10-12 k) in water (3×25 L). The contents were then transferred to an Erlenmeyer flask and 24% ammonia (200 mL) added. After 2 h, the pH was adjusted to 10.5, and the reaction was stirred overnight. Excess ammonia was removed by dialysis (MWCO 10-12 k) in water (8×25 L), and the entire contents lyophilized to yield the aminodextran 5.75 g (78%, based on a aminodextran MW of 185 k) as a white fluffy substance. Elemental analysis was used to make a rough estimate the molecular weight, amine incorporation, and amount of incorporated divinylsulfone. (Found C, 39.86; H, 6.26; N, 0.16; S, 3.08%. Dextran 150k, ~22DVS—NH$_2$, ~160DVS—OH, and ~720H$_2$O requires C, 39.55; H, 6.60; N, 0.16; S, 3.07%).

Example C2

Polymer Synthesis

The following example illustrates how the Mannose 50 mol % copolymer was prepared. Other polymer preparations are summarized in Table 3. The monosaccharides used and their quantities are summarized in Table 4.

Stock solutions (100 mg/ml) of Allyl-saccharides (AS) and N-(3-aminopropyl)methacrylamide hydrochloride (NAMH) were prepared in PBS (50 mM, pH 7.4).

Potassium peroxodisulfate (PPS) (150 mg) was dissolved in PBS buffer (50 mM, pH 7.4; 7.8 ml) in a screw-capped plastic tube. To this solution was added in the following order Allyl α-D-Mannopyranoside (Allylsaccharide; AS) (2.20 ml; 220 mg), 2-hydroxyethylacrylate (HEA) (110 µl), N-(3-aminopropyl)methacrylamide hydrochloride (NAMH) (89 µl) and N,N,N',N'-tetramethylethylenediamine (TMEDA) (100 µl). The mixture was purged with nitrogen for 5 min to remove dissolved oxygen. Polymerization was carried overnight at room temperature in an orbital shaker. The reaction mixture was filtered and precipitated in methanol (100 ml). The polymer was collected by centrifugation (4000 rpm, 3 min) and then washed with methanol (3×10 ml). The final obtained polymer pellet was dried overnight in an exiccator.

TABLE 3

| Calcd. saccharide molar fraction | AS (ml) | HEA (µl) | NAMH (µl) | PBS (ml) | PPS (mg) | TMEDA (µl) | Polymer yield (mg) |
|---|---|---|---|---|---|---|---|
| Mannose 10% | 0.44 | 203 | 89 | 9.56 | 150 | 100 | 95 |
| Mannose 30% | 1.32 | 157 | 89 | 8.68 | 150 | 100 | 119 |
| Mannose 50% | 2.20 | 110 | 89 | 7.80 | 150 | 100 | 164 |
| Mannose 70% | 3.08 | 64 | 89 | 6.92 | 150 | 100 | 171 |
| Mannose 90% | 3.96 | 17 | 89 | 6.04 | 150 | 100 | 152 |
| GlcNAc 10% | 0.75 | 203 | 89 | 9.56 | 150 | 100 | 114 |
| GlcNAc 30% | 2.26 | 157 | 89 | 8.68 | 150 | 100 | 122 |
| GlcNAC 50% | 3.77 | 110 | 89 | 7.80 | 150 | 100 | 149 |
| GlcNAc 70% | 5.28 | 64 | 89 | 6.92 | 150 | 100 | 159 |
| GlcNAc 90% | 6.80 | 17 | 89 | 6.04 | 150 | 100 | 160 |
| Glucose 10% | 0.44 | 203 | 89 | 9.56 | 150 | 100 | 98 |
| Glucose 30% | 1.32 | 157 | 89 | 8.68 | 150 | 100 | 105 |

TABLE 3-continued

| Calcd. saccharide molar fraction | AS (ml) | HEA (μl) | NAMH (μl) | PBS (ml) | PPS (mg) | TMEDA (μl) | Polymer yield (mg) |
|---|---|---|---|---|---|---|---|
| Glucose 50% | 2.20 | 110 | 89 | 7.80 | 150 | 100 | 158 |
| Glucose 70% | 3.08 | 64 | 89 | 6.92 | 150 | 100 | 160 |
| Glucose 90% | 3.96 | 17 | 89 | 6.04 | 150 | 100 | 162 |
| Galactose 10% | 0.44 | 203 | 89 | 9.56 | 150 | 100 | 95 |
| Galactose 30% | 1.32 | 157 | 89 | 8.68 | 150 | 100 | 119 |
| Galactose 50% | 2.20 | 110 | 89 | 7.80 | 150 | 100 | 164 |
| Galactose 70% | 3.08 | 64 | 89 | 6.92 | 150 | 100 | 171 |
| Galactose 90% | 3.96 | 17 | 89 | 6.04 | 150 | 100 | 152 |

TABLE 4

| Allyl-α-D-Mannose | Allyl-α-D-N-Acetyl-glucosamine | Allyl-α-D-Glucose | Allyl-α-D-Galactose |
|---|---|---|---|
| 10% | 10% | 10% | 10% |
| 30% | 30% | 30% | 30% |
| 50% | 50% | 50% | 50% |
| 70% | 70% | 70% | 70% |
| 90% | 90% | 90% | 90% |

Example C3

ELLA Assay on Polymers of C2

TBS buffer used in the ELLA assay was 20 mM TRIS, 150 mM NaCl, 1.25 mM $CaCl_2$ (mimicking physiological calcium concentration), pH 7.4.

A 96-well microtiter plate was coated, overnight at 5° C., with two columns of each of the antigens (polymers from Example C3, aminodextran from Example C1) (100 μl, 100 μg/ml) in TBS. Residual binding sites were blocked by the addition of 0.5% (w/v) BSA in TBS (150 μl). The wells were then washed (2×200 μl TBS). Dilutions of Glucose (from 100 mM to 0 mM) in biotinylated MBL (2 μg/ml) were added to a total volume of 100 μl. After incubation for 2 h, the plate was emptied and washed (2×200 μl TBS).

Streptavidin-HRP 0.1% (v/v) (100 μl) in TBS was added and incubated for 1 h. Plates were then emptied and washed (3×200 μl TBS). The presence of HRP was visualized by the addition of substrate solution (1 mg o-phenylene dihydrochloride) and quenched after 2 min with 2 N sulfuric acid. Colour development was determined by reading the absorbance at 490 nm, with background subtraction at 630 nm. The results are shown in the graphs in FIG. 1. High absorptions correspond to binding of MBL to the ligand. Baseline absorption corresponds to no binding of MBL to the ligand.

Figure 5:
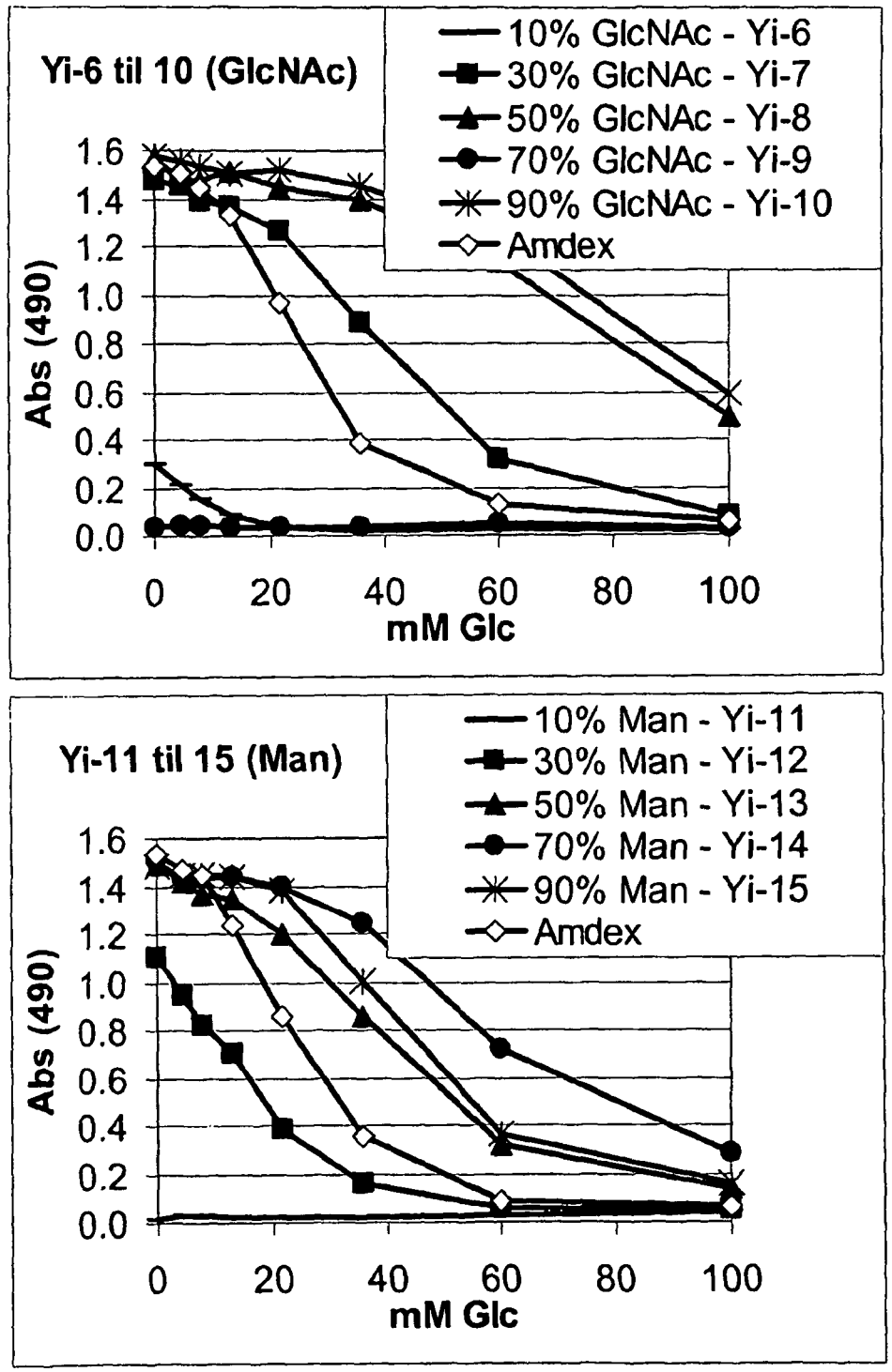
FIG. 5 shows the ELLA assay results obtained in Example C3.
Figure 5:
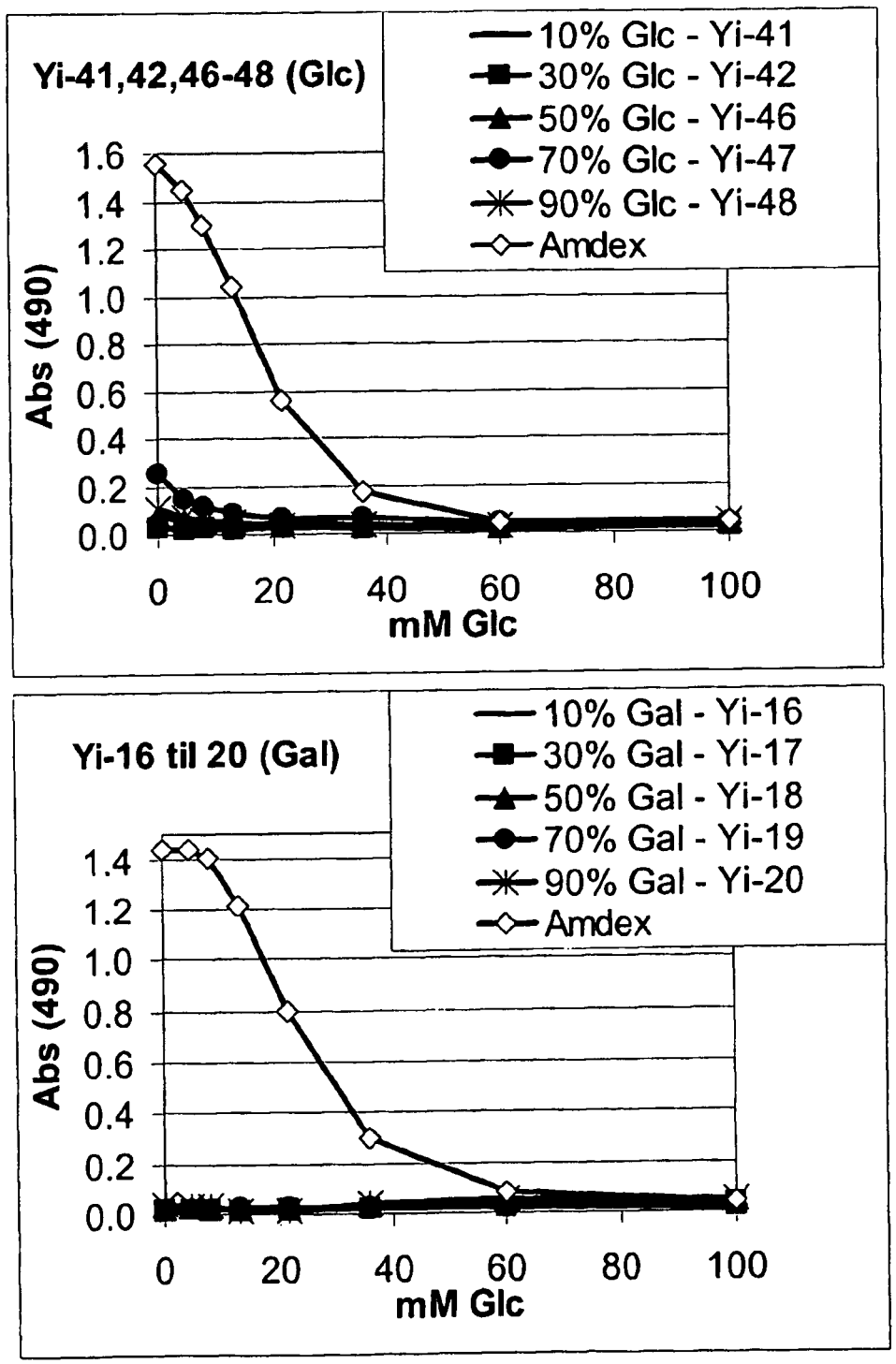

As shown in FIG. 5, the monomeric saccharide unit needs to have higher affinity to MBL than glucose ($IC_{50}$ ~18 mM) and is preferably mannose ($IC_{50}$ ~8 mM) or N-acetyl-glucosamine ($IC_{50}$ ~6 mM). Lower affinity saccharide monomer units, such as galactose ($IC_{50}$ ~36 mM), do not give MBL binding at physiological calcium concentrations.

The best results were achieved using a co-polymer with between 30% and 50% mannose monomer units, since these copolymers were most easily inhibited (steepest slope) in the range of 0 to 10 mM glucose. Therefore, in an optimization step (Example C4) a range of mannose co-polymers having mannose monomer unit contents within the range of 30% to 50% were synthesized.

Example C4

Polymer Synthesis (Optimisation)

Figure 6:
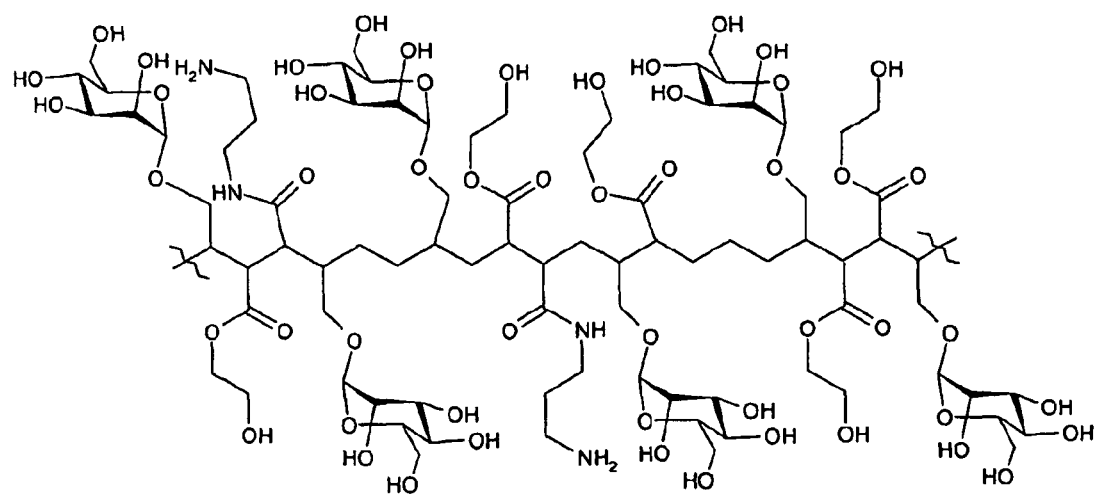
FIG. 6 shows the reactants of Example C4.
Figure 7:
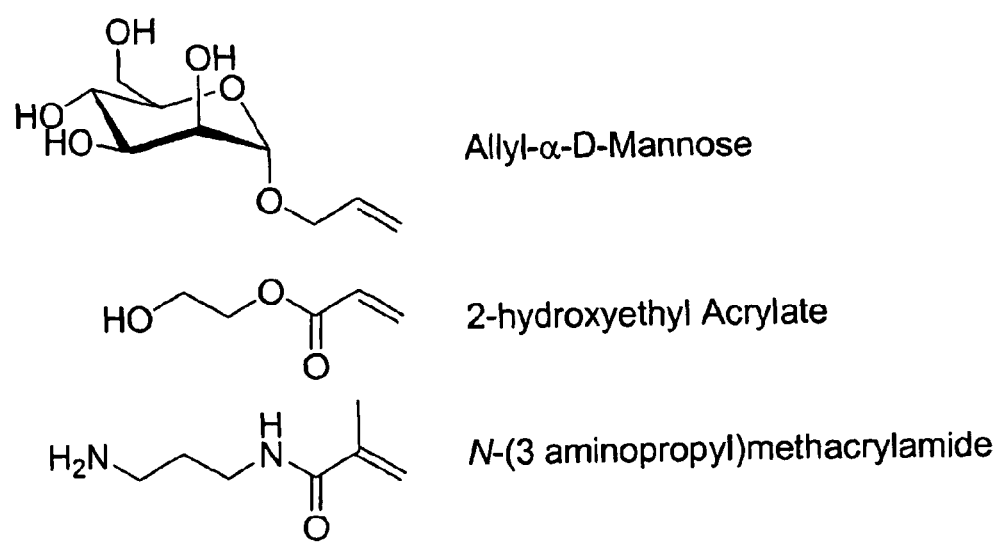
FIG. 7 shows an example of a polymer product of Example C4.

The preparation method was as for Example C2. The polymer preparations are summarized in Table 5. The reactants are shown in FIG. 6. An example of a polymer product is shown in FIG. 7.

TABLE 5

| Calcd. saccharide molar fraction | AS (ml) | HEA (μl) | NAMH (μl) | PBS (ml) | PPS (mg) | TMEDA (μl) | Polymer yield (mg) |
|---|---|---|---|---|---|---|---|
| Mannose 30% | 1.32 | 157 | 89 | 8.68 | 150 | 100 | 111 |
| Mannose 35% | 1.54 | 145 | 89 | 8.46 | 150 | 100 | 148 |
| Mannose 40% | 1.76 | 134 | 89 | 8.24 | 150 | 100 | 151 |
| Mannose 45% | 1.98 | 122 | 89 | 8.02 | 150 | 100 | 149 |
| Mannose 50% | 2.20 | 110 | 89 | 7.80 | 150 | 100 | 158 |

Example C5

ELLA Assay (Optimisation) on Polymers of Example C5

An ELLA assay was carried out as described in Example C3. The results are shown in FIG. 8.

Figure 8:
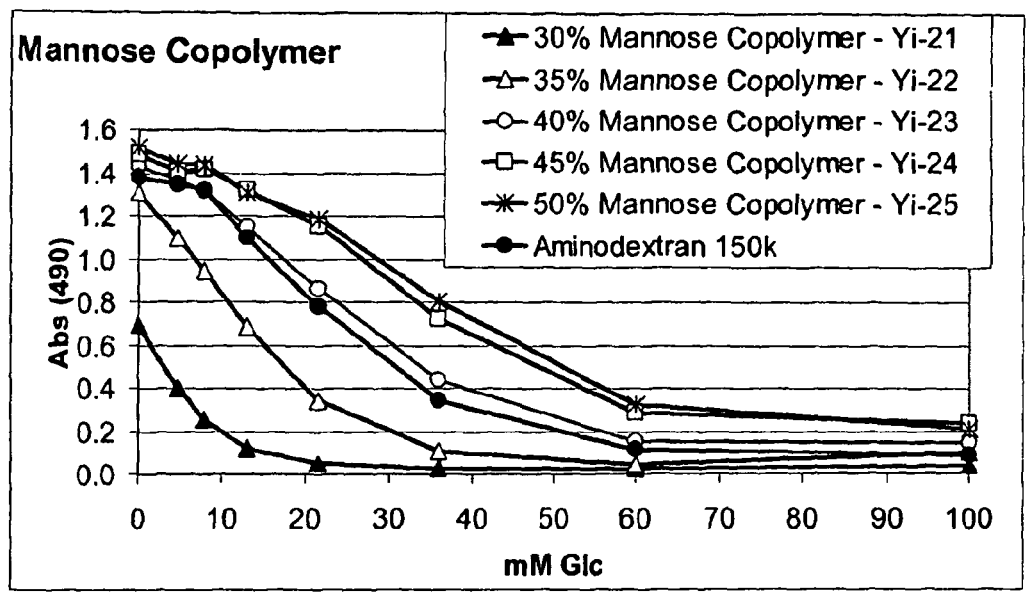
FIG. 8 shows the ELLA assay results obtained in Example C5.

FIG. 8 shows that 35 mol % Mannose co-polymer is an optimized ligand. The binding is as strong as aminodextran to MBL at 0 mM glucose, but is more easily inhibited than binding of aminodextran. From the inhibition curves, it is possible to calculate an $IC_{50}$ value for aminodextran and the optimized ligand (Table 6). (The $IC_{50}$ value is only valid for this particular assay.)

TABLE 6

| $IC_{50}$ | Glucose (mM) |
|---|---|
| Aminodextran | 23 |
| 35 mol % Man Copolymer | 13 |

The invention claimed is:

1. A sensor for the detection or measurement of a carbohydrate analyte in fluid, the sensor comprising components of a competitive binding assay the readout of which is a detectable or measurable optical signal retained by a material that permits diffusion of the analyte but not the assay components, the assay components comprising:
   a carbohydrate binding molecule labeled with one of a proximity based signal generating/modulating moiety pair wherein the carbohydrate binding molecule specifically binds to the carbohydrate analyte; and
   a carbohydrate analogue capable of competing with the analyte for binding to the carbohydrate binding molecule, the carbohydrate analogue being a flexible water-soluble polymer comprising:
   polymerized residues of monomer units, the monomer unit residues bearing pendant carbohydrate or carbohydrate mimetic moieties and pendant moieties which are the other of the proximity based signal generating/modulating moiety pair; and/or
   co-polymerised residues of first monomer units and second monomer units, the first monomer unit residues bearing pendant carbohydrate or carbohydrate mimetic moieties and the second monomer unit residues bearing pendant moieties which are the other of the proximity based signal generating/modulating moiety pair;
   where said polymer has a non-carbohydrate backbone.

2. A sensor as claimed in claim 1, comprising a copolymer of said first and second monomer units polymerized from a reaction mixture, wherein the second monomer units are present in the reaction mixture in an amount of 5 to 15 mol %.

3. A sensor as claimed in claim 1, wherein the carbohydrate moieties are selected from optionally derivatised mannose, maltose, isomaltose, glucose, sophorose and/or 2-acetylglucosamine.

4. A sensor as claimed in claim 1, wherein the proximity based signal generating/modulating moieties are linked to amine, acid, alcohol, alkyne, azide and/or sulphone functional groups of the monomer units or the second monomer units.

5. A sensor as claimed in claim 1, wherein the proximity based signal generating/modulating moieties are energy donors or energy acceptors.

6. A sensor as claimed in claim 1, further comprising polymerized residues of third monomer units not bearing carbohydrate or carbohydrate mimetic moieties or proximity based signal generating/modulating moieties.

7. A sensor as claimed in claim 6, wherein the third monomer units are present in the reaction mixture in an amount of 0 to 80 mol %.

8. A sensor as claimed in claim 6, wherein the third monomer units contain hydrophilic groups.

9. A sensor as claimed in claim 8, wherein the third monomer units comprise 2-hydroxyethylacrylate, vinyl pyrrolidone, MMA, HEMA, vinyl alcohol and/or ethylene glycol.

10. A sensor as claimed in claim 1, wherein the average polymer molecular weight is in the range of 20 to 250 kDa.

11. A sensor as claimed in claim 1, wherein the carbohydrate analyte is glucose and the polymer is capable of competing with glucose at physiological calcium concentrations.

12. A sensor as claimed in claim 11, wherein the assay is capable of measuring blood glucose at concentrations over at least part of the range of 0 to 35 mM glucose.

13. A sensor as claimed in claim 1, wherein the carbohydrate binding molecule is a lectin.

14. A sensor as claimed in claim 13, wherein the carbohydrate binding molecule is mannose binding lectin or Concanavalin A.

15. A sensor as claimed in claim 1, wherein the components of the assay are retained by a shell or matrix material.

16. A sensor as claimed in claim 15, wherein the retaining material is biodegradable.

17. A method of preparing a sensor as claimed in claim 1, the method comprising at least one of phase separation (coacervation), solvent evaporation, extraction, spray drying, spray coating, spray chilling, rotary disk atomisation, fluid bed coating, coextrusion and pan coating.

18. A method of detecting a carbohydrate analyte using a sensor as claimed in claim 1, comprising implantation of the sensor into the skin of a mammal and transdermal detection or measurement of carbohydrate analyte using external optical means.

19. A method of detecting a carbohydrate analyte using a sensor as claimed in claim 1, comprising transdermal detection or measurement of a carbohydrate analyte using external optical means by illumination of a said sensor present in or below the skin of a mammal.

20. A sensor as claimed in claim 1, wherein the polymer is unbranched.

21. A sensor as claimed in claim 1, wherein the first monomer unit residues and the second monomer unit residues are different in structure not just because of their pendant moieties.

22. A sensor as claimed in claim 1, wherein the polymer has less than 10% double bonds in the backbone.

23. A sensor as claimed in claim 1, wherein the polymer is formed by addition polymerization.

24. A sensor as claimed in claim 1, wherein the polymer comprises polymerized residues of allyl α-D-mannopyranoside, 2-hydroxyethylacrylate and labeled N-(3-aminopropyl) methacrylamide.

* * * * *